United States Patent
Boon et al.

(10) Patent No.: US 12,207,609 B2
(45) Date of Patent: **\*Jan. 28, 2025**

(54) BRILLIANT WHITE CAULIFLOWER

(71) Applicant: SEMINIS VEGETABLE SEEDS, INC., St. Louis, MO (US)

(72) Inventors: Meinardus Petrus Boon, Scharwoude (NL); Franciscus van den Bosch, Kesteren (NL); Gerard Koorevaar, Ede (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,242

(22) Filed: Oct. 24, 2023

(65) Prior Publication Data
US 2024/0188523 A1    Jun. 13, 2024

Related U.S. Application Data

(60) Continuation of application No. 17/509,852, filed on Oct. 25, 2021, now Pat. No. 11,832,571, which is a division of application No. 16/283,313, filed on Feb. 22, 2019, now Pat. No. 11,166,425, which is a continuation of application No. 15/387,249, filed on Dec. 21, 2016, now Pat. No. 10,251,361, which is a continuation of application No. 14/095,590, filed on Dec. 3, 2013, now Pat. No. 9,560,814, which is a continuation of application No. 13/302,923, filed on Nov. 22, 2011, now Pat. No. 8,633,350, which is a continuation of application No. 11/905,611, filed on Oct. 2, 2007, now Pat. No. 8,084,669.

(60) Provisional application No. 60/848,632, filed on Oct. 3, 2006.

(51) Int. Cl.
*A01H 6/20* (2018.01)
*A01H 5/00* (2018.01)
*A01H 5/10* (2018.01)
*C12Q 1/6895* (2018.01)

(52) U.S. Cl.
CPC .............. *A01H 6/203* (2018.05); *A01H 5/00* (2013.01); *A01H 5/10* (2013.01); *C12Q 1/6895* (2013.01)

(58) Field of Classification Search
None
See application file for complete search history.

(56) References Cited

U.S. PATENT DOCUMENTS 5,492,547 A    2/1996    Johnson
7,750,207 B2   7/2010    Wu et al.

FOREIGN PATENT DOCUMENTS

WO    WO 2006/131291 A1    12/2006

OTHER PUBLICATIONS

Arus et al., "Marker-assisted selection," *Chapter 19 of Plant Breeding, Principles and Prospects*, First Edition 1993, pp: 314-331 (with cover page) (1993) (London, UK), in prior U.S. Appl. No. 17/509,852.
Cebula, "The Effect of Pot Size and Transplant Age on the Yield and Quality of White, Green and Romanesco Cauliflower Curds," *Vegetable Crops Research Bulletin*, 70:101-110 (2009), in prior U.S. Appl. No. 11/905,611.
Chagnon et al., "Development of a Cauliflower Leaf Tying Machine," written for presentation at the CSAE/SCGR 2003 Meeting Montréal, Québec, Jul. 6-9, 2003, in prior U.S. Appl. No. 14/095,590.
Cutcliffe, "Cultivar and Spacing Effects on Incidence of Hollow Stem in Broccoli," *Can. J. Plant Sci.*, 55:867-869 (1975), in prior U.S. Appl. No. 11/905,611.
Cutcliffe, "Effects of Plant Spacing and Nitrogen on Incidence of Hollow Stem in Broccoli," *Can. J. Plant Sci.*, 52:833-834 (1972), in prior U.S. Appl. No. 11/905,611.
Dickson et al., "Persistent White Curd and Other Curd Characters of Cauliflower," *J. Amer. Soc. Hor. Sci.*, 105(4):533-535 (1980), in prior U.S. Appl. No. 11/905,611.
Dickson, "Male Sterile Persistent White Curd Cauliflower NY 7642 A and Its Maintainer NY 7642B," *HortScience*, 20(5):957 (1985), in prior U.S. Appl. No. 11/905,611.
Dufault, "Dynamic Relationships between Field Temperatures and Broccoli Head Quality," *J. Amer. Soc. Hort. Sci.*, 121(4):705-710 (1996), in prior U.S. Appl. No. 11/905,611.
Fehr, Principles of Cultivar Development, vol. 1, pp. 2-3 (1987), in prior U.S. Appl. No. 11/905,611.
International Search Report, International Application PCT/US07/21191 (published as WO 2008/042392), dated Sep. 9, 2008, in prior U.S. Appl. No. 11/905,611.
Jansen et al., "High Resolution of Quantitative Traits Into Multiple Loci Via Interval Mapping" *Genetics*, vol. 136, pp. 1447-1455 (Apr. 1994) (Washington, DC), in prior U.S. Appl. No. 17/509,852.
Jansen et al., "Genotype-by-environment interaction in genetic mapping of multiple quantitative trait loci," *Theor Appl Genet.* vol. 91, pp. 33-37 (1995) (Berlin, Germany), in prior U.S. Appl. No. 17/509,852.

(Continued)

*Primary Examiner* — Mykola V. Kovalenko
*Assistant Examiner* — David R Byrnes
(74) *Attorney, Agent, or Firm* — Arnold & Porter Kaye Scholer LLP

(57) ABSTRACT

The present invention includes cauliflowers with enhanced whiteness and methods for obtaining such cauliflowers. The present invention also provides reagents that can be used in methods for obtaining such cauliflowers.

17 Claims, 5 Drawing Sheets
(1 of 5 Drawing Sheet(s) Filed in Color)
Specification includes a Sequence Listing.

(56) References Cited

OTHER PUBLICATIONS

Jourdan et al., "Improved protoplast culture and stability of cytoplasmic traits in plants regenerated from leaf protoplasts of cauliflower (Brassica oleracea ssp. bolrytis), " *Plant Cell. Tissue and Organ Culture, 21*:227-236 (1990), in prior U.S. Appl. No. 11/905,611.

Kieffer et al., "Characterisation of the Morphological Features of the Cauliflower Curd," Abstracts of Oral Papers & Posters, ISHS Symposium on Brassicas, Ninth Crucifer Genetics Workshop, p. 111, Lisbon, Portugal (Nov. 15-19, 1994), in prior U.S. Appl. No. 11/905,611.

Kieffer et al., "Level of Control of Cauliflower Curd Explant for Shoot Regeneration," Abstracts of Oral Papers & Posters, ISHS Symposium on Brassicas, Ninth Crucifer Genetics Workshop, p. 109, Lisbon, Portugal (Nov. 15-19, 1994), in prior U.S. Appl. No. 11/905,611.

Kieffer et al., "The Rapid Mass Production of Cauliflower Propagules from Fractionated and Graded Curd," Abstracts of Oral Papers & Posters, ISHS Symposium on Brassicas, Ninth Crucifer Genetics Workshop, p. 37, Lisbon, Portugal (Nov. 15-19, 1994), in prior U.S. Appl. No. 11/905,611.

Kieffer et al., "The Rapid Mass Production of Cauliflower Propagules from Fractionated and Graded Curd," Abstracts of Oral Papers & Posters, ISHS Symposium on Brassicas, Ninth Crucifer Genetics Workshop, p. 110, Lisbon, Portugal (Nov. 15-19, 1994), in prior U.S. Appl. No. 11/905,611.

Kruglyak et al., "A Nonparametric Approach for Mapping Quantitative Trait Loci," *Genetics*, vol. 139, pp. 1421-1428, (Mar. 1995) (Washington, DC), in prior U.S. Appl. No. 17/509,852.

Lander et al., "Mapping Mendelian Factors Underlying Quantitative Traits Using RFLP Linkage Maps," *Genetics*, vol. 121, pp. 185-199 (Jan. 1989) (Washington, DC), in prior U.S. Appl. No. 17/509,852.

Marino et al., "Acid phosphatase polymorphism within and among populations of Cauliflower (Brassica oleracea var botrytis), " *Genetics and Molecular Biology, 25*(1):81-84 (2002), in prior U.S. Appl. No. 11/905,611.

Michelmore et al., "Identification of markers linked to disease-resistance genes by bulked segregant analysis: A rapid method to detect markers in specific genomic regions by using segregating populations," *Genetics*, vol. 88, pp. 9828-9832 (Nov. 1991) (Washington, DC), in prior U.S. Appl. No. 17/509,852.

Pinetree Garden Seeds, "Minute Man Cauliflower (F1 Hybrid 55 days)," retrieved Feb. 25, 2015, at: www[dot]superseeds[dot]com/vegetables/column1/cauliflower/minutemancauliflower[dot]html, in prior U.S. Appl. No. 14/095,590.

Qaderi et al., "Morphological and physiological responses of canola (Brassica napus) siliquas and seeds to UVB and $CO_2$ under controlled environment conditions," *Environmental and Experimental Botany, 60*:428-437 (2007), in prior U.S. Appl. No. 11/905,611.

Reiter et al., "Global and local genome mapping in *Arabidopsis thaliana* by using recombinant inbred lines and random amplified polymorphic DNAs," *Genetics*, vol. 89, pp: 1477-1481 (Feb. 1992) (Washington, DC), in prior U.S. Appl. No. 17/509,852.

Ross, "Embryo Culture in the Production of Disease-Resistant Brassicas," *Tissue Culture Methods for Plant Pathologists*, Halsted Press, pp. 255-258 (1980), in prior U.S. Appl. No. 13/302,923.

Shattuck et al., "Environmental Stability of Yield and Hollow Stem in Broccoli (Brassica oleracea var. Italica)," *Can J. Plant Sci., 66*:683-688 (1986), in prior U.S. Appl. No. 11/905,611.

Siegers Seed Company, Vegetable Seeds, "Hybrid Cauliflower," Oct. 25, 2005. Retrieved at: www.siegers.com/shop/kind.asp?kind_id=U, in prior U.S. Appl. No. 14/095,590.

Slater et al., "Chapter 2: Plant Tissue Culture," *Plant Biotechnology: the Genetic Manipulation of Plants*, Oxford University Press 2008, pp. 37-53 (2008), in prior U.S. Appl. No. 13/302,923.

Supplementary European Search Report, European Application No. 07 83 9168 (published as EP 2 083 614), dated Sep. 25, 2009, in prior U.S. Appl. No. 11/905,611.

Tanksley et al., *Molecular mapping plant chromosome, Chromosome structure and function: Impact of new concepts*, J. P. Gustafson and R. Appels (eds.), Plenum Press, New York, pp. 157-173 (1988), in prior U.S. Appl. No. 11/905,611.

W.H. Perron Dominion Seed House, "Hyb. Minuteman," retrieved Feb. 25, 2015, at: www.dominionseedhouse.com/en/9556hybminuteman.html, in prior U.S. Appl. No. 14/095,590.

Walton, "Molecular Markers: Which Ones to Use?" *Seed World*, pp. 22-29 (Jul. 1993) (Grand Forks, ND), in prior U.S. Appl. No. 17/509,852.

Zeng, "Precision Mapping of Quantitative Trait Loci," *Genetics* vol. 136, pp. 1457-1468 (Apr. 1994) (Washington, DC), in prior U.S. Appl. No. 17/509,852.

Zum Felde et al., "Genotype X Environment Interactions, Heritability, and Trait Correlations of Sinapate Ester Content in Winter Rapeseed (Brassica napus L.)," *Crop Science, 46*(5):2195-2199 (2006), in prior U.S. Appl. No. 11/905,611.

Figure 1
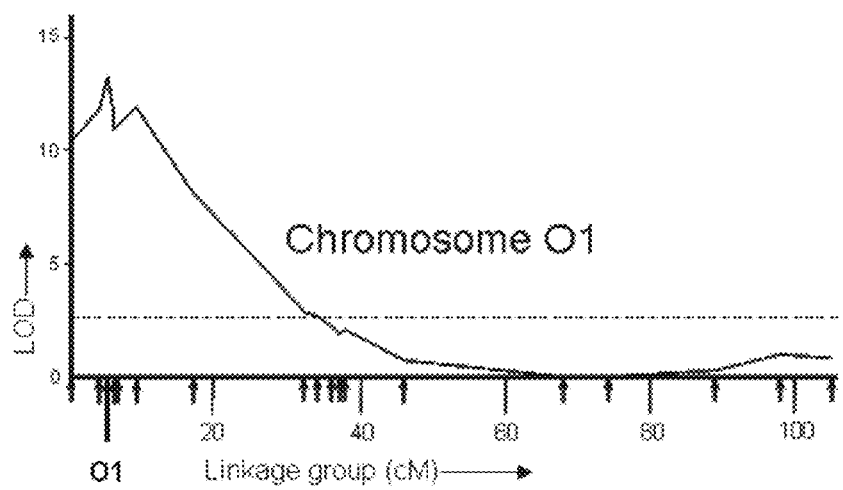
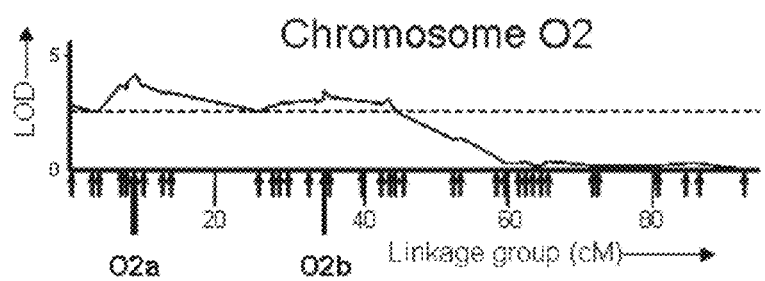
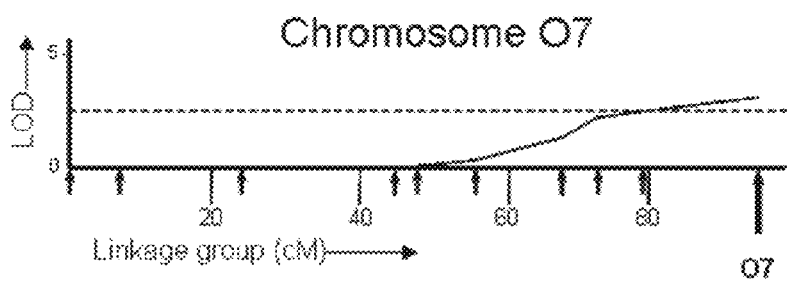
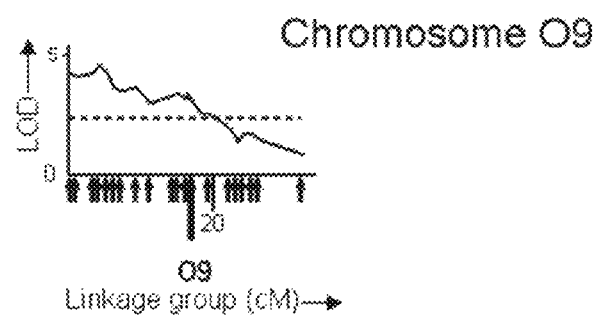

Figure 2
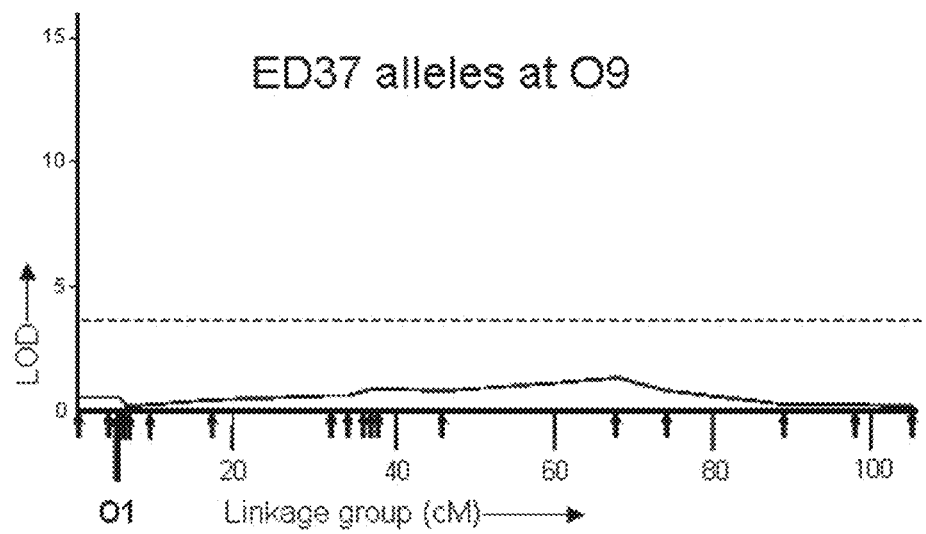
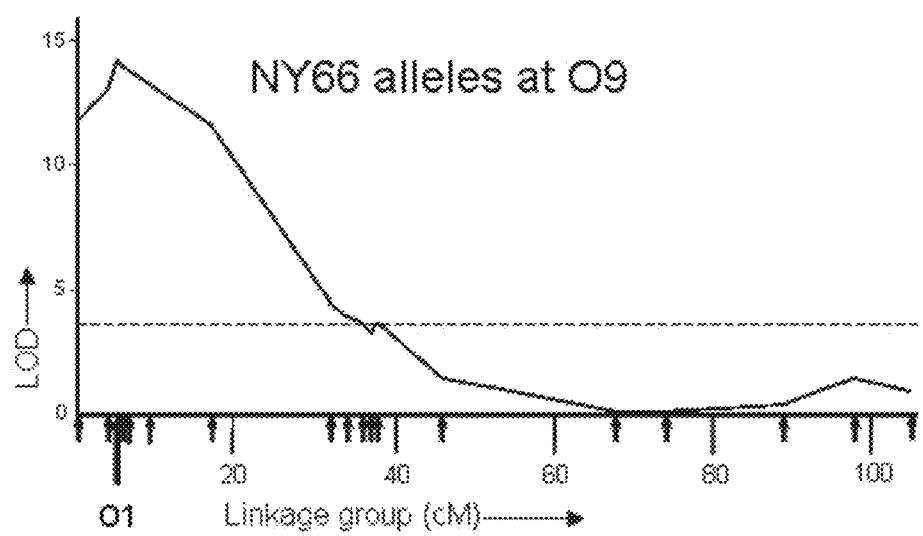

Figure 3
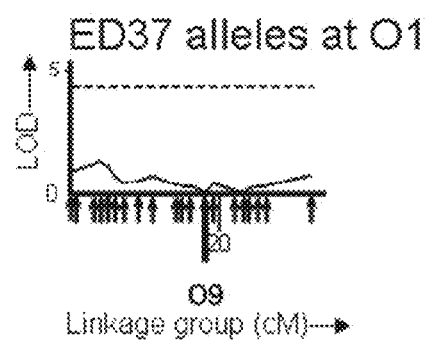
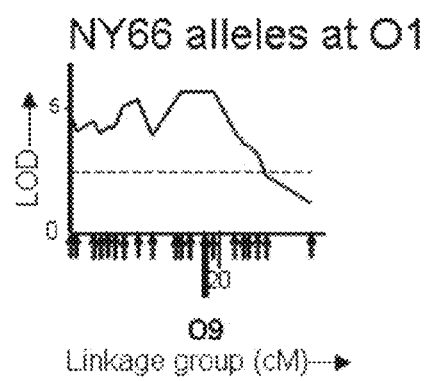

```
........TTATA
CGTCATGTNNNNTAGGTTTTACAAGTTAAGCTTAGTCGGTNNNNNNNNCATGTNNNNNNNNNGTGGTAGTTGAATTTTAGTTNNNNNNNNCACCAACCCTATATGTTTATAC
TCCCTCCGT

..........TTAGGT
TTTAAATATAAGTAGTTTTAGTAAAAGAGTTGTTCACAATATAAGTAATTATATATTCAATGCATTTTTTTATTGGATATTGTGTGACCAATGAAATAATGTTAGGT
TTTAATAA

..........AACATTTT
TTGGTTGAATTAATTGGTTAAATGATATATATTCTTTTAAATAATAAATAATAAATTTCTAAATATTCGTATTTTTAAGCAAAACTACTACTTAGAAACGGATGGAGTAACATTTTCTTC
CCTTCCAATATAACAAATGAATAAATATCTCACCAACTGATAGTAACAAAAAAAAACAAAAAAAATCTCACCACTGATTAATTACATGTAAACGCAAATG
TCGTTAGTCTAGGTGTAGGATGGTCATTGTGTGCTTAAGAAGGGGTCCTACCTTTGTGGGAAAAGCTTCGGTGCACGTGTCCGTGAGTTCTGTCCTCTTATGTGCCA
TGAACCCACACACGTCGTTCCTCCGTCATTTCTTGACTTCTCATTGGCTGGAAACCACAAGATTCCACACACCAAGATTCCGTGAAACCACACCGTTAAATGCTTCCGTTACTCTTGA
GTTGTTCTTTTCTACTATTGCATTTTTTTTATTAGAGGGAGAAAGACACTTCTCACACGCCTCTAACCTAATGAGATTACGTGTGTGCGATTTTCCGATCTTTTGCT
TGTTCCCAAGACATATATAAAGTAGATTTTCATTCNTGTACGNTCAAATCTCGAACCTATG
```

Figure 4

SEQUENCE LISTING

```
Sequence total quantity: 19
SEQ ID NO: 1            moltype = DNA  length = 544
FEATURE                 Location/Qualifiers
misc_feature            56
                        note = single nucleotide polymorphism between donor NY66
                        and ED37 recipient
source                  1..544
                        mol_type = genomic DNA
                        organism = Brassica oleracea
```

-continued

```
SEQUENCE: 1
caatcgacag cttcagcaaa gtcactctct ttcagaaaga gtgagccttt ctcggccagc    60
tcgtctgcga actcaagcgt cttctcactc tctagggttt gctcgagttc cgaagccgaa   120
gctggtgctt tttcttcaac catggctcaa gcttgagaat gggtttctg ggtaggttcg    180
aaatcaaaac gagaacgtta gctgagaaag aggaagcgtt tatggctcta cttgtagtac   240
cctaaaaggc taaaacccttt tcttctttgt ttttttcttc tagaaatgtt gatctaggaa   300
gaagaacatt tctatttttg acatgtgatg ttttttatgca ttttaatgag tactgcgtgt   360
cgttttagac tattttttgac atcatgatgt tttatgcgtt ttaacgggaa catcgagtcg   420
tttgtcatat ttttaatatg tgtggttgct aatagctttt agacgwagag acgaagaagc   480
catcatcgac ttgtaaagtc gaaaccttttt gtgtgttctg tcatctctgt ctccactcga   540
tggc                                                               544

SEQ ID NO: 2               moltype = DNA  length = 23
FEATURE                    Location/Qualifiers
misc_feature               1..23
                           note = Primer/Probe sequence
source                     1..23
                           mol_type = other DNA
                           organism = synthetic construct
SEQUENCE: 2
agcttcagca aagtcactct ctt                                           23

SEQ ID NO: 3               moltype = DNA  length = 23
FEATURE                    Location/Qualifiers
misc_feature               1..23
                           note = Primer/Probe Sequence
source                     1..23
                           mol_type = other DNA
                           organism = synthetic construct
SEQUENCE: 3
agagtgagaa gacgcttgag ttc                                           23

SEQ ID NO: 4               moltype = DNA  length = 15
FEATURE                    Location/Qualifiers
misc_feature               1..15
                           note = Primer/Probe Sequence
source                     1..15
                           mol_type = other DNA
                           organism = synthetic construct
SEQUENCE: 4
cgagctggcc gagaa                                                    15

SEQ ID NO: 5               moltype = DNA  length = 16
FEATURE                    Location/Qualifiers
misc_feature               1..16
                           note = Primer/Probe Sequence
source                     1..16
                           mol_type = other DNA
                           organism = synthetic construct
SEQUENCE: 5
acgagctgac cgagaa                                                   16

SEQ ID NO: 6               moltype = DNA  length = 394
FEATURE                    Location/Qualifiers
misc_feature               187
                           note = Single nucleotide polymorphism between NY66 donor
                              and ED37 recipient
source                     1..394
                           mol_type = genomic DNA
                           organism = Brassica oleracea
SEQUENCE: 6
tcatgattta gagggagttt ccatcaacta caaggtcaag gtaactccgg atctcccgga    60
gacgtgcatc cagccccttc aaagcagtaa gtttcgcagt gacctggtgc aaaatacaat   120
ttcacattat ttcagttttc aaacagtaac cattttgtca atataacaac tttgcaagaa   180
cagcgacatg aatcctccaa gcaccagcca tcatgatttc acgactaaag ggatgataat   240
gaaacgttga aatattgtga agtcaaatac ctcagtcgca agggtactga tcgttgtgtc   300
tttcacatcc cttagcaaat gctccacgcc tattagagaa cgataataaa gcaattacgt   360
cagatgactt tcctcaatcc aatcataaaa gacg                               394

SEQ ID NO: 7               moltype = DNA  length = 31
FEATURE                    Location/Qualifiers
misc_feature               1..31
                           note = Primer/Probe Sequence
source                     1..31
                           mol_type = other DNA
                           organism = synthetic construct
SEQUENCE: 7
tcagttttca aacagtaacc attttgttca t                                  31
```

```
SEQ ID NO: 8                moltype = DNA   length = 19
FEATURE                     Location/Qualifiers
misc_feature                1..19
                            note = Primer/Probe Sequence
source                      1..19
                            mol_type = other DNA
                            organism = synthetic construct
SEQUENCE: 8
atgatggctg gtgcttgga                                                      19

SEQ ID NO: 9                moltype = DNA   length = 15
FEATURE                     Location/Qualifiers
misc_feature                1..15
                            note = Primer/Probe Sequence
source                      1..15
                            mol_type = other DNA
                            organism = synthetic construct
SEQUENCE: 9
aacagcgaca tgaat                                                          15

SEQ ID NO: 10               moltype = DNA   length = 18
FEATURE                     Location/Qualifiers
misc_feature                1..18
                            note = Primer/Probe Sequence
source                      1..18
                            mol_type = other DNA
                            organism = synthetic construct
SEQUENCE: 10
aagaacagcg atatgaat                                                       18

SEQ ID NO: 11               moltype = DNA   length = 585
FEATURE                     Location/Qualifiers
variation                   9
                            note = n is a, c, g, or t
variation                   14
                            note = n is a, c, g, or t
variation                   21..22
                            note = n is a, c, g, or t
variation                   51..57
                            note = n is a, c, g, or t
variation                   98
                            note = n is a, c, g, or t
misc_feature                418
                            note = Single nucleotide polymorphism between NY66 donor
                             and ED37 recipient
source                      1..585
                            mol_type = other DNA
                            organism = Brassica oleracea
SEQUENCE: 11
ctatcttang acancccatg nnttgcatat acaaattgat atatcatttc nnnnnnngtt         60
ttttgacaaa tcattgtgaa ggatgtgtgg aaggaatnca caggctggcc attgaacgat        120
atggagagtt cgtataagtt catggtgaag catgttcagc tatggaaagt tgcattccac        180
accacatctc ccaaatgggt tcactcttgc tatctagcag ccattgcagc gtattacgca        240
aaggaagtcg aggcgggttt gatggagtac aagccagaga ttatcatcag tgttcatcct        300
ctgatgcaac acattccctt gtgggttctc aaatgcgcaa agctacaaaa gagagtcctc        360
tttgtcactg tcattactga tctcaacact tgtcatccta catggtatat ataataaata        420
ggccggttta ttatattctc tgagagatgc tggctgctgg tttgatattt tatcctgtat        480
ggtttaggtt tcatccaggg gtgaaccgat gctattgccc gtctcaagaa gtggcgaaaa        540
gggcgttgtt tgatgggcta gatgagtctc aagtccgtgt gtggg                        585

SEQ ID NO: 12               moltype = DNA   length = 24
FEATURE                     Location/Qualifiers
misc_feature                1..24
                            note = Primer/Probe Sequence
source                      1..24
                            mol_type = other DNA
                            organism = synthetic construct
SEQUENCE: 12
ccatagtcca taactgtttc atgc                                                24

SEQ ID NO: 13               moltype = DNA   length = 20
FEATURE                     Location/Qualifiers
misc_feature                1..20
                            note = Primer/Probe Sequence
source                      1..20
                            mol_type = other DNA
                            organism = synthetic construct
SEQUENCE: 13
cacaggcaaa ccaaacacac                                                     20
```

```
SEQ ID NO: 14          moltype = DNA  length = 878
FEATURE                Location/Qualifiers
variation              9..12
                       note = n is a, c, g, or t
variation              41..49
                       note = n is a, c, g, or t
variation              55..64
                       note = n is a, c, g, or t
variation              85..91
                       note = n is a, c, g, or t
variation              423
                       note = n is a, c, g, or t
variation              854
                       note = n is a, c, g, or t
variation              861
                       note = n is a, c, g, or t
source                 1..878
                       mol_type = genomic DNA
                       organism = Brassica oleracea
SEQUENCE: 14
cgtcatgtnn nntaggtttt acaagttaag cttagtcggt nnnnnnnnnc atgtnnnnnn       60
nnnngtggta gttgaatttt agttnnnnnn ncaccaaccc tatatgtttt atactccctc      120
cgttttaaaa tataagtagt tttagtaaaa agagtttgtt tcacaatata agtaatttat      180
atatttcaat gcattttttt tattggatat tgtgtgacca atgaaataat gttaggtttt      240
taataattgg ttgaattaat tggttaaatg atatattctt ttaaataata aatttctaaa      300
tattcgtatt tttaagcaaa actacttaca attagaaacg gatggagtaa cattttcttc      360
ccttccaata taacaaatga ataaatatct caccaactga tagtaacaaa aaaaaaaaaa      420
aancaaaaaa aaaaaaaaat ctcaccactg attaattaca tgtaaacgca aatgtcgttt      480
agtctaggtg tagtaggatg gtgcattgtg cttaagaagg ggtcctacct ttgtgggaaa      540
agcttcggtg cacgtgtctt gcgtgagttc ttgtcctctt atgtgccatg aacccacaca      600
caccgtcgtt tccttccgtc cattttcttt gactctcatt ggcttggaag tccgtgaaac      660
cacaagattc cacacaccgt taaatggctc cgttactctt gagttgttct tttcttattc      720
tactattgca tttttttttat tagagggaga aagacacttc tcacacgcct ctaacctaaa      780
tgagattacg tctgtcggat tttccgatct tttgcttgtt cccaagacat atatataaag      840
tagattttca ttcntgtacg ntcaaatctc gacctatg                              878

SEQ ID NO: 15          moltype = DNA  length = 25
FEATURE                Location/Qualifiers
misc_feature           1..25
                       note = Primer/Probe Sequence
source                 1..25
                       mol_type = other DNA
                       organism = synthetic construct
SEQUENCE: 15
ttttgttttg ttttatgcat gtttc                                              25

SEQ ID NO: 16          moltype = DNA  length = 25
FEATURE                Location/Qualifiers
misc_feature           1..25
                       note = Primer/Probe Sequence
source                 1..25
                       mol_type = other DNA
                       organism = synthetic construct
SEQUENCE: 16
gtaatgcttc aagatatgga gaatg                                              25

SEQ ID NO: 17          moltype = DNA  length = 663
FEATURE                Location/Qualifiers
variation              11
                       note = n is a, c, g, or t
variation              47..55
                       note = n is a, c, g, or t
variation              62..70
                       note = n is a, c, g, or t
variation              93..97
                       note = n is a, c, g, or t
misc_feature           268
                       note = Single nucleotide polymorphism between NY66 donor
                       and ED37 recipient
source                 1..663
                       mol_type = genomic DNA
                       organism = Brassica oleracea
SEQUENCE: 17
cttgacgagc natcccttc tcacttatt ctccttgcaa acccttnnnn nnnnngcatt        60
annnnnnnnn cgcatcaggt ttcaccccag ttnnnnnaca ttttcttgaa aacctcaaac      120
gcctggtccg ctcttccata cgagcagaac cccgtgatca tcgtattaca gctcaccgtt      180
gtctctccaa acccatttct aagcatctct ccgtatagtt ccctagccag cacaacttcg      240
cctctttca agtgcgcatg tatcatcaca ttgtaagtaa actcgttagg ccgcatccct      300
```

```
ttctccatca tctcaaacca cagcttcctc gcgctcccga accaccccat ctcgcatagc    360
ccatggatca tcgtggtgta aacgaccctg tcaggcgcat agcctctctc tttaagattg    420
ttaaacacac aaaacgcctc gcgctgcttc tgattcttgc acagccccct gataatctcc    480
tggtaggtat aaatactcgg ggaatggttc caggcaatca tcgtgtggag aatctccgac    540
atacaagcgt agttcccaat cttacaaaag ccagaaatca atttggcata gacaacatgt    600
cctggatcaa gcccttgttt caaaactttc ttgagtagct cgtaccsttc tgaaacctct    660
cac                                                                  663

SEQ ID NO: 18          moltype = DNA  length = 20
FEATURE                Location/Qualifiers
misc_feature           1..20
                       note = Primer/Probe Sequence
source                 1..20
                       mol_type = other DNA
                       organism = synthetic construct
SEQUENCE: 18
agaagggtac atccccaagg                                                 20

SEQ ID NO: 19          moltype = DNA  length = 19
FEATURE                Location/Qualifiers
misc_feature           1..19
                       note = Primer/Probe Sequence
source                 1..19
                       mol_type = other DNA
                       organism = synthetic construct
SEQUENCE: 19
ctttgtgcga cggtgagag                                                  19
```

BRILLIANT WHITE CAULIFLOWER

CROSS REFERENCE TO RELATED APPLICATIONS

This application is a continuation application of U.S. patent application Ser. No. 17/509,852, filed Oct. 25, 2021 (now U.S. Pat. No. 11,832,571, issued on Dec. 5, 2023), which is a divisional of U.S. patent application Ser. No. 16/283,313, filed Feb. 22, 2019 (now U.S. Pat. No. 11,166,425, issued on Nov. 9, 2021), which is a continuation of U.S. patent application Ser. No. 15/387,249, filed Dec. 21, 2016 (now U.S. Pat. No. 10,251,361, issued Apr. 9, 2019), which is a continuation of U.S. patent application Ser. No. 14/095,590, filed Dec. 3, 2013 (now U.S. Pat. No. 9,560,814, issued Feb. 7, 2017), which is a continuation of U.S. patent application Ser. No. 13/302,923, filed Nov. 22, 2011 (now U.S. Pat. No. 8,633,350, issued Jan. 21, 2014), which is a continuation of U.S. patent application Ser. No. 11/905,611, filed Oct. 2, 2007 (now U.S. Pat. No. 8,084,669, issued Dec. 27, 2011), which claims the benefit under 35 U.S.C. § 119 of U.S. Provisional Application No. 60/848,632, filed Oct. 3, 2006, all of which are incorporated by reference in their entireties herein.

FIELD OF THE INVENTION

The present invention includes cauliflowers with enhanced whiteness and methods for obtaining such cauliflowers. The present invention also provides reagents that can be used in methods for obtaining such cauliflowers.

INCORPORATION OF THE SEQUENCE LISTING

The Sequence Listing is hereby incorporated by reference in its entirety, including the file named P30720US07 ST26, which is 34,009 bytes in size and was created on Dec. 10, 2023, which is herein incorporated by reference in its entirety.

BACKGROUND OF THE INVENTION

Cauliflower (*Brassica oleracea* Var. *botrytis*) is a crop of the Cruciferae/Brassicaceae, or Mustard, family that also includes crop plants such as broccoli, cabbage, kale, turnips and mustard. Cauliflower plants for commercial production are typically started in a greenhouse from seeds. After about 35 to 40 days cauliflower seedlings are transplanted to the field, where they are grown for another 40-300 days, depending on variety and local growing conditions, to maturity and harvest. During the curd initiation phase the meristem of the cauliflower plant forms a generative bud; this bud will develop into the mature flower head, or curd, which is the harvested and marketed part of the plant.

Whiteness of the curd is a desirable trait in cauliflower. Curds of conventional cauliflower varieties turn from creamy white to yellow when exposed to light, particularly the natural sunlight of field production. Creamy white curds that have yellow patches or are totally yellow are undesirable and declassify the product. Maintenance of the whitest possible curd in cauliflower is achieved by a combination of variety selection and the cultural practice of covering or tying leaves together over the curds. These cultural practices are labor intensive, and expensive. Covering is initiated at about the point that the curd reaches a few inches in diameter. Workers are required to enter the fields at this bud stage, and manually fold the large outer leaves of the plant over the head of the cauliflower to prevent the sun exposure during curd development. It is typically about one week from tying to harvest. The plants must be examined during this period to see that the tying is secure, as even small amounts of sunlight coming through cracks in the leaves can result in discolored patches on the curd. Examination of the plants is also needed to assess when the curd is ready to be cut and harvested. Overmature curds also develop other undesirable traits. For instance it may become loose and ricey, at which stage the quality of the cauliflower is lost.

Plant breeding has been used to develop several varieties of cauliflower that display a curd with enhanced whiteness. Even in these varieties, however, exposure to the sun will discolor the curd, affecting the commercial value of the crop.

In recent years, breeders have also evaluated the "persistent white" trait in cauliflower, i.e., a curd that will not discolor from white to creamy when exposed to sunlight. Descriptions of this trait can be found, for example, in Dickson, et al, *Persistent White Curd and Other Curd Characters of Cauliflower* (1980) Amer. Soc. Hor. Sci 105 (4):533-535; and Dickson, M. H., *Male Sterile Persistent White Curd Cauliflower NY 7642A and its Maintainer NY 7642B* (October 1985) HortScience, Vol. 20(5), 957. These authors describe the development of male sterile persistent white curd cauliflower NY 7642A and its maintainer NY7642B, though certain unfavorable traits were linked to a persistent white character, namely, riciness, bracting and low curd density. Persistent white varieties have continued to have problems with these quality traits, making them poor candidates for commercial production.

Thus, there is a need for improved cauliflower varieties having a white quality trait but lacking the unfavorable traits present in previous persistent white varieties.

SUMMARY OF THE INVENTION

The present invention includes and provides cauliflowers having a curd color score of less than about C4 on a Ctifl cauliflower color chart, where the curd color is obtained after growth without covering.

The present invention further includes and provides cauliflower plants having brilliant white curd and favorable curd characteristics, where the brilliant white curd color persists when the cauliflower plant is exposed to sunlight in the absence of covering.

The present invention also includes and provides cauliflower plants having brilliant white curd, where the brilliant white curd color persists when the cauliflower plant is exposed to sunlight in the absence of covering, and where the curd has a diameter of about 15 cm and a weight of at least 700 grams.

The present invention also includes and provides a container of cauliflower seeds where cauliflower plants from greater than 50% of the seeds have a curd having a curd color score of less than C4 on a Ctifl color chart.

The present invention also includes and provides a cauliflower plant having a genome, where the genome comprises a genetic locus derived from a cauliflower plant selected from the group consisting of CEL/1857, PI183214, 901203-2/FREMONT, NY6633, NY3339, 90331, BCSS, HOCE, and PWCE, where the genetic locus contains one or more alleles of a quantitative trait locus genetically linked to the complement of a marker nucleic acid molecule selected from the group consisting of QTLO1, QTLO2a, QTLO2b, QTLO7, and QTLO9.

The present invention also includes and provides a cauliflower plant having at least four brilliant white alleles selected from the group consisting of QTLO1, QTLO2a, QTLO2b, QTLO7, and QTLO9.

The present invention also includes and provides a cauliflower plant having brilliant white curd and at least one brilliant white allele selected from the group consisting of QTLO1. QTLO2a, QTLO2b, QTLO7, and QTLO9.

The present invention includes and provides seed of the cauliflower variety CLP/NY6633/9/Fre, where a representative sample of seed of the variety has been deposited under NCIMB Accession No. 41432.

The present invention includes and provides seed of the cauliflower variety CLP/NY6633, where a representative sample of seed of the variety has been deposited under NCIMB Accession No. 41430.

The present invention also includes and provides seed of the cauliflower variety BCSS/CLP/NY6633, where a representative sample of seed of the variety has been deposited under NCIMB Accession No. 41431.

The present invention also includes and provides seed of the cauliflower variety CLP/NY6633/9/Fre/CLP/NY6633/HOCE, where a representative sample of seed of the variety has been deposited under NCIMB Accession No. 41433.

The present invention also includes and provides methods of introgressing at least one brilliant white curd allele into a cauliflower plant comprising: a) crossing a plant from a first cauliflower line as a first parent having at least one white curd allele with a second cauliflower plant as a second parent to form a segregating population, b) screening the segregating population for a member having at least one white curd allele with a nucleic acid molecule capable of identifying a white allele at QTLO1, QTLO2a, QTLO2b, QTLO7, or QTLO9; and c) selecting a cauliflower plant that contains at least one white allele at QTLO1, QTLO2a, QTLO2b, QTLO7, or QTLO9 for further crossing.

The present invention further includes and provides methods of producing a cauliflower having a brilliant white curd comprising: a) selecting a plant from cauliflower line CEL/1857 as a first parent; b) crossing the first parent with a second cauliflower plant from a cauliflower line selected from the group consisting of CEL/1857, PI183214, 901203-2/FREMONT, NY6633, NY3339, 90331, BCSS, HOCE, and PWCE as a second parent; c) growing cauliflower seed produced by the cross to yield a progeny cauliflower plant; d) determining a color score on the Ctifl color chart for the progeny cauliflower plant; e) if the progeny cauliflower plant has a color score equal or greater than C4 on the Ctifl color chart, repeating steps b) through d) using the progeny cauliflower plant in each successive round as the first parent until a cauliflower plant having a color score less than C4 on the Ctifl color chart has been produced, thereby producing a cauliflower having a brilliant white curd.

The present invention also includes and provides methods of producing a cauliflower having a brilliant white curd comprising a) selecting a plant from a cauliflower line selected from the group consisting of CEL/1857, PI183214, 901203-2/FREMONT, NY6633, NY3339, 90331, BCSS, HOCE, and PWCE as a first parent; b) crossing the first parent with a second cauliflower plant selected from the group consisting of CEL/1857, PI183214, 901203-2/FREMONT, NY6633, NY3339, 90331, BCSS, HOCE, and PWCE as a second parent to form a segregating population, c) screening the segregating population with one or more nucleic acid markers capable of detecting a white allele at QTLO1, QTLO2a, QTLO2b, QTLO7, and QTLO9; d) selecting from the segregating population a cauliflower plant that is homozygous for a white allele at QTLO1, QTLO2a, QTLO2b, QTLO7, and QTLO9, e) determining a color score on the Ctifl color chart for the selected cauliflower plant, f) if the selected cauliflower plant has a color score equal or greater than C4 on the Ctifl color chart, repeating steps b) through d) using the selected cauliflower plant in each successive round as the first parent until a cauliflower plant having a color score less than C4 on the Ctifl color chart has been produced, thereby producing a cauliflower having a brilliant white curd.

CERTAIN EMBODIMENTS

Embodiment 1. A cauliflower having a curd color score of less than about C4 on a Ctifl cauliflower color chart, wherein said curd color is obtained after growth without covering.

Embodiment 2. A cauliflower according to embodiment 1, wherein said cauliflower exhibits a curd color of less than about C4 on the Ctifl color chart under a condition selected from the group consisting of: at the time of harvest where the cauliflower was not subject to leaf tying, after five days of storage at 5° C., and after five days of storage at ambient temperature.

Embodiment 3. A cauliflower according to embodiment 2, wherein said cauliflower has a curd color score of less than or equal to about C2 on a Ctifl color chart.

Embodiment 4. A part of a cauliflower of embodiment 1 having a curd color score of less than or equal to about C3 relative to a Ctifl color chart.

Embodiment 5. A plant part of embodiment 4, wherein said plant is selected from the group consisting of a seed, curd, and leaf.

Embodiment 6. A plant part of embodiment 4, wherein said plant part is selected from the group consisting of pollen and an ovule.

Embodiment 7. A cell derived from a plant of embodiment 1.

Embodiment 8. A protoplast derived from a plant of embodiment 1.

Embodiment 9. A tissue culture of cells obtained from the cauliflower plant of embodiment 1.

Embodiment 10. The tissue culture of embodiment 9, wherein the cells are from a tissue selected from the group consisting of leaf, pollen, embryo, root, root tip, anther, flower, bud, curd and meristem.

Embodiment 11. A seed from the cauliflower plant of embodiment 1.

Embodiment 12. A cauliflower plant having brilliant white curd and favorable curd characteristics, wherein the brilliant white curd color persists when the cauliflower plant is exposed to sunlight in the absence of covering.

Embodiment 13. The cauliflower plant of embodiment 12, wherein the brilliant white curd color persists when the cauliflower plant is exposed to sunlight in the absence of self covering.

Embodiment 14. The cauliflower plant of embodiment 12 having a curd color score of less than C4 on a Ctifl color chart.

Embodiment 15. The cauliflower plant of embodiment 12, having a color score less than or equal to about C2 on the Ctifl color chart.

Embodiment 16. A plant part of the cauliflower plant of embodiment 12.

Embodiment 17. The plant part of embodiment 16, further defined as pollen, a protoplast, an ovule or a cell.

Embodiment 18. A tissue culture of cells obtained from the cauliflower plant of embodiment 12.

Embodiment 19. The tissue culture of embodiment 18, wherein the cells are from a tissue selected from the group consisting of leaf, pollen, embryo, root, root tip, anther, flower, bud, curd and meristem.

Embodiment 20. A seed from the cauliflower plant of embodiment 12.

Embodiment 21. A cauliflower plant having brilliant white curd, wherein the brilliant white curd color persists when the cauliflower plant is exposed to sunlight in the absence of covering, and wherein the curd has a diameter of about 15 cm and a weight of at least 700 grams.

Embodiment 22. The cauliflower plant of embodiment 21, wherein the brilliant white curd color persists when the cauliflower plant is exposed to sunlight in the absence of self covering.

Embodiment 23. The cauliflower plant of embodiment 21, having a color score less than C4 on the Ctifl color chart.

Embodiment 24. The cauliflower plant of embodiment 21, having a color score less than or equal to about C2 on the Ctifl color chart.

Embodiment 25. A plant part of the cauliflower plant of embodiment 21.

Embodiment 26. The plant part of embodiment 25, further defined as pollen, a protoplast, an ovule or a cell.

Embodiment 27. A tissue culture of cells obtained from the cauliflower plant of embodiment 21.

Embodiment 28. The tissue culture of embodiment 27, wherein the cells are from a tissue selected from the group consisting of leaf, pollen, embryo, root, root tip, anther, flower, bud, curd and meristem.

Embodiment 29. A seed from the cauliflower plant of embodiment 21.

Embodiment 30. A container of cauliflower seeds wherein cauliflower plants from greater than 50% of said seeds have a curd having a curd color score of less than C4 on a Ctifl color chart.

Embodiment 31. The container of cauliflower seeds of embodiment 30, wherein said container comprises at least 100 seeds.

Embodiment 32. The container of cauliflower seeds of embodiment 30, wherein said container comprises at least 1,000 seeds.

Embodiment 33. The container of cauliflower seeds of embodiment 30, wherein said container is selected from the group consisting of a bag, a box, a packet, a pouch, a foil, and a pail.

Embodiment 34. The container of cauliflower seeds of embodiment 30, wherein cauliflower plants grown from greater than 75% of said seeds have a curd having a curd color score of less than C4 on a Ctifl color chart.

Embodiment 35. The container of cauliflower seeds of embodiment 30, wherein cauliflower plants grown from greater than 85% of said seeds have a curd having a curd color score of less than C4 on a Ctifl color chart.

Embodiment 36. The container of cauliflower seeds of embodiment 30, wherein cauliflower plants grown from greater than 95% of said seeds have a curd having a curd color score of less than C4 on a Ctifl color chart.

Embodiment 37. A cauliflower plant having a genome, wherein said genome comprises a genetic locus derived from a cauliflower plant selected from the group consisting of CEL/1857, PI183214, 901203-2/FREMONT, NY6633, NY3339, 90331, BCSS, HOCE, and PWCE, wherein said genetic locus contains one or more alleles of a quantitative trait locus genetically linked to the complement of a marker nucleic acid molecule selected from the group consisting of QTLO1, QTLO2a, QTLO2b, QTLO7, and QTLO9.

Embodiment 38. The cauliflower plant of embodiment 37, wherein at least 12.5% of said genome is derived from a cauliflower plant selected from the group consisting of CEL/1857, PI183214, 901203-2/FREMONT, NY6633, NY3339, 90331, BCSS, HOCE, and PWCE.

Embodiment 39. The cauliflower plant of embodiment 38, wherein at least 25% of said genome is derived from a cauliflower plant selected from the group consisting of CEL/1857, PI183214, 901203-2/FREMONT, NY6633, NY3339, 90331, BCSS, HOCE, and PWCE.

Embodiment 40. The cauliflower plant of embodiment 39, wherein at least 50% of said genome is derived from a cauliflower plant selected from the group consisting of CEL/1857, PI183214, 901203-2/FREMONT, NY6633, NY3339, 90331, BCSS, HOCE, and PWCE.

Embodiment 41. The cauliflower plant of embodiment 37, wherein said genetic locus is located between about 0 and about 50 centimorgans from said complement of said marker nucleic acid.

Embodiment 42. The cauliflower plant of embodiment 41, wherein said genetic locus is located between about 0 and about 40 centimorgans from said complement of said marker nucleic acid.

Embodiment 43. The cauliflower plant of embodiment 42, wherein said genetic locus is located between about 0 and about 25 centimorgans from said complement of said marker nucleic acid.

Embodiment 44. The cauliflower plant of embodiment 43, wherein said genetic locus is located between about 0 and about 10 centimorgans from said complement of said marker nucleic acid.

Embodiment 45. The cauliflower plant of embodiment 44, wherein said genetic locus is located between about 0 and about 5 centimorgans from said complement of said marker nucleic acid.

Embodiment 46. The cauliflower plant of embodiment 45, wherein said genetic locus is located between about 0 and about 3 centimorgans from said complement of said marker nucleic acid.

Embodiment 47. The cauliflower plant of embodiment 37, wherein said marker nucleic acid exhibits a LOD score for brilliant white curd trait of greater than 2.0 for said allele.

Embodiment 48. The cauliflower plant of embodiment 47, wherein said marker nucleic acid exhibits a LOD score for brilliant white curd trait of greater than 2.5 for said allele.

Embodiment 49. The cauliflower plant of embodiment 48, wherein said marker nucleic acid exhibits a LOD score for brilliant white curd trait of greater than 3.0 for said allele.

Embodiment 50. The cauliflower plant of embodiment 49, wherein said marker nucleic acid exhibits a LOD score for brilliant white curd trait of greater than 3.5 for said allele.

Embodiment 51. The cauliflower plant of embodiment 37, wherein said genetic locus contains two or more alleles of a quantitative trait locus genetically linked to the complement of a marker nucleic acid molecule selected from the group consisting of QTLO1, QTLO2a, QTLO2b, QTLO7, and QTLO9.

Embodiment 52. The cauliflower plant of embodiment 51, wherein said genetic locus contains three or more alleles of a quantitative trait locus genetically linked to the complement of a marker nucleic acid molecule selected from the group consisting of QTLO1, QTLO2a, QTLO2b, QTLO7, and QTLO9.

Embodiment 53. The cauliflower plant of embodiment 52, wherein said genetic locus contains four or more alleles of a quantitative trait locus genetically linked to the complement of a marker nucleic acid molecule selected from the group consisting of QTLO1, QTLO2a, QTLO2b, QTLO7, and QTLO9.

Embodiment 54. The cauliflower plant of embodiment 53, wherein said genetic locus contains five alleles of a quantitative trait locus genetically linked to the complement of a marker nucleic acid molecule selected from the group consisting of QTLO1, QTLO2a, QTLO2b. QTLO7, and QTLO9.

Embodiment 55. A cauliflower plant having at least four brilliant white alleles selected from the group consisting of QTLO1, QTLO2a, QTLO2b, QTLO7, and QTLO9.

Embodiment 56. The cauliflower plant of embodiment 55, wherein said cauliflower plant has five brilliant white alleles selected from the group consisting of QTLO1, QTLO2a, QTLO2b, QTLO7, and QTLO9.

Embodiment 57. The cauliflower plant of embodiment 55, wherein said cauliflower plant also has a brilliant white curd.

Embodiment 58. A cauliflower plant having brilliant white curd and at least one brilliant white allele selected from the group consisting of QTLO1, QTLO2a, QTLO2b, QTLO7, and QTLO9.

Embodiment 59. The cauliflower plant of embodiment 58, having at least two brilliant white alleles selected from the group consisting of QTLO1, QTLO2a, QTLO2b, QTLO7, and QTLO9.

Embodiment 60. The cauliflower plant of embodiment 59, having at least three brilliant white alleles selected from the group consisting of QTLO1, QTLO2a, QTLO2b, QTLO7, and QTLO9.

Embodiment 61. The cauliflower plant of embodiment 60, having at least four brilliant white alleles selected from the group consisting of QTLO1, QTLO2a, QTLO2b, QTLO7, and QTLO9.

Embodiment 62. The cauliflower plant of embodiment 61, having five brilliant white alleles selected from the group consisting of QTLO1, QTLO2a, QTLO2b, QTLO7, and QTLO9.

Embodiment 63. A seed of the cauliflower variety CLP/NY6633/9/Fre, wherein a representative sample of seed of the variety has been deposited under NCIMB Accession No. 41432.

Embodiment 64. A plant grown from the seed of embodiment 63.

Embodiment 65. A plant part of the plant of embodiment 64.

Embodiment 66. The plant part of embodiment 65, further defined as pollen, a protoplast, an ovule or a cell.

Embodiment 67. A tissue culture of cells obtained from the plant of embodiment 64.

Embodiment 68. The tissue culture of embodiment 65, wherein the cells are from a tissue selected from the group consisting of leaf, pollen, embryo, root, root tip, anther, flower, bud, curd and meristem.

Embodiment 69. A seed of the cauliflower variety CLP/NY6633, wherein a representative sample of seed of the variety has been deposited under NCIMB Accession No. 41430.

Embodiment 70. A plant grown from the seed of embodiment 69.

Embodiment 71. A plant part of the plant of embodiment 70.

Embodiment 72. The plant part of embodiment 71, further defined as pollen, a protoplast, an ovule or a cell.

Embodiment 73. A tissue culture of cells obtained from the plant of embodiment 70.

Embodiment 74. The tissue culture of embodiment 73, wherein the cells are from a tissue selected from the group consisting of leaf, pollen, embryo, root, root tip, anther, flower, bud, curd and meristem.

Embodiment 75. A seed of the cauliflower variety BCSS/CLP/NY6633, wherein a representative sample of seed of the variety has been deposited under NCIMB Accession No. 41431.

Embodiment 76. A plant grown from the seed of embodiment 75.

Embodiment 77. A plant part of the plant of embodiment 76.

Embodiment 78. The plant part of embodiment 77, further defined as pollen, a protoplast, an ovule or a cell.

Embodiment 79. A tissue culture of cells obtained from the plant of embodiment 76.

Embodiment 80. The tissue culture of embodiment 79, wherein the cells are from a tissue selected from the group consisting of leaf, pollen, embryo, root, root tip, anther, flower, bud, curd and meristem.

Embodiment 81. A seed of the cauliflower variety CLP/NY6633/9/Fre/CLP/NY6633/HOCE, wherein a representative sample of seed of the variety has been deposited under NCIMB Accession No. 41433.

Embodiment 82. A plant grown from the seed of embodiment 81.

Embodiment 83. A plant part of the plant of embodiment 82.

Embodiment 84. The plant part of embodiment 83, further defined as pollen, a protoplast, an ovule or a cell.

Embodiment 85. A tissue culture of cells obtained from the plant of embodiment 82.

Embodiment 86. The tissue culture of embodiment 85, wherein the cells are from a tissue selected from the group consisting of leaf, pollen, embryo, root, root tip, anther, flower, bud, curd and meristem.

Embodiment 87. A method of introgressing at least one brilliant white curd allele into a cauliflower plant comprising
  a) crossing a plant from a first cauliflower line as a first parent having at least one white curd allele with a second cauliflower plant as a second parent to form a segregating population,
  b) screening said segregating population for a member having at least one white curd allele with a nucleic acid molecule capable of identifying a white allele at QTLO1, QTLO2a, QTLO2b, QTLO7, or QTLO9; and
  c) selecting a cauliflower plant that contains at least one white allele at QTLO1, QTLO2a, QTLO2b, QTLO7, or QTLO9 for further crossing.

Embodiment 88. The method according to embodiment 87, wherein said method further comprises determining a color score on the Ctifl color chart for the selected cauliflower plant.

Embodiment 89. The method according to embodiment 87, wherein said method further comprises crossing said selected cauliflower plant to a plant from a persistent white cauliflower line.

Embodiment 90. The method according to embodiment 87, wherein the cauliflower plants selected at step c) have favorable curd characteristics.

Embodiment 91. The method according to embodiment 87, wherein the cauliflower plants selected at step c) have a curd diameter of about 15 cm and a curd weight of at least 700 grams.

Embodiment 92. The method of embodiment 87, wherein said nucleic acid molecule is selected from the group consisting of SEQ ID NO: 1, 6, 11, 14, 17, complements of, or fragments thereof having at least 15 nucleotides.

Embodiment 93. The method of embodiment 87, wherein said nucleic acid molecule is capable of detecting a nucleic acid sequence that is present on a linkage group selected from the group consisting of linkage group 1, 2, 7, or 9 within 100 kb of said white curd allele.

Embodiment 94. The method of embodiment 93, wherein said nucleic acid molecule is capable of detecting a nucleic acid sequence that is present on a linkage group selected from the group consisting of linkage group 1, 2, 7, or 9 within 50 kb of said white curd allele.

Embodiment 95. The method of embodiment 94, wherein said nucleic acid molecule is capable of detecting a nucleic acid sequence that is present on a linkage group selected from the group consisting of linkage group 1, 2, 7, or 9 within 25 kb of said white curd allele.

Embodiment 96. The method of embodiment 95, wherein said white curd allele is also present in a cauliflower line selected from the group consisting of CLP/NY6633, CLP/NY6633/9/Fre, BCSS/CLP/NY6633, and CLP/NY6633/9/Fre/CLP/NY6633/HOCE.

Embodiment 97. The method of embodiment 87, wherein said member has at least two white curd alleles.

Embodiment 98. The method of embodiment 97, wherein said member has at least three white curd alleles.

Embodiment 99. The method of embodiment 98, wherein said member has at least four white curd alleles.

Embodiment 100. The method of embodiment 99, wherein said member has five white curd alleles.

Embodiment 101. A method of producing a cauliflower having a brilliant white curd comprising
a) selecting a plant from cauliflower line CEL/1857 as a first parent
b) crossing the first parent with a second cauliflower plant from a cauliflower line selected from the group consisting of CEL/1857, PI183214, 901203-2/FREMONT, NY6633, NY3339, 90331, BCSS, HOCE, and PWCE as a second parent,
c) growing cauliflower seed produced by said cross to yield a progeny cauliflower plant,
d) determining a color score on the Ctifl color chart for the progeny cauliflower plant,
e) if the progeny cauliflower plant has a color score equal or greater than C4 on the Ctifl color chart, repeating steps b) through d) using the progeny cauliflower plant in each successive round as the first parent until a cauliflower plant having a color score less than C4 on the Ctifl color chart has been produced,
thereby producing a cauliflower having a brilliant white curd.

Embodiment 102. The method according to embodiment 101, wherein the progeny cauliflower plants of step c) have favorable curd characteristics.

Embodiment 103. The method according to embodiment 101, wherein the progeny cauliflower plants of step c) have a curd diameter of about 15 cm and a curd weight of at least 700 grams.

Embodiment 104. The method of embodiment 101, wherein said cauliflower contains at least one white allele selected from the group consisting of QTLO1, QTLO2a, QTLO2b, QTLO7, and QTLO9.

Embodiment 105. The method of embodiment 101, wherein said cauliflower contains at least two whites alleles selected from the group consisting of QTLO1, QTLO2a, QTLO2b, QTLO7, and QTLO9.

Embodiment 106. The method of embodiment 105, wherein said cauliflower contains at least three whites alleles selected from the group consisting of QTLO1, QTLO2a, QTLO2b, QTLO7, and QTLO9.

Embodiment 107. The method of embodiment 106, wherein said cauliflower contains at least four whites alleles selected from the group consisting of QTLO1, QTLO2a, QTLO2b, QTLO7, and QTLO9.

Embodiment 108. The method of embodiment 107, wherein said cauliflower contains five whites alleles at QTLO1, QTLO2a, QTLO2b, QTLO7, and QTLO9.

Embodiment 109. A method of producing a cauliflower having a brilliant white curd comprising
a) selecting a plant from a cauliflower line selected from the group consisting of CEL/1857, PI183214, 901203-2/FREMONT, NY6633, NY3339, 90331, BCSS, HOCE, and PWCE as a first parent
b) crossing the first parent with a second cauliflower plant selected from the group consisting of CEL/1857, PI183214, 901203-2/FREMONT, NY6633, NY3339, 90331, BCSS, HOCE, and PWCE as a second parent to form a segregating population,
c) screening said segregating population with one or more nucleic acid markers capable of detecting a white allele at QTLO1, QTLO2a, QTLO2b, QTLO7, and QTLO9;
d) selecting from said segregating population a cauliflower plant that is homozygous for a white allele at QTLO1, QTLO2a, QTLO2b, QTLO7, and QTLO9,
e) determining a color score on the Ctifl color chart for the selected cauliflower plant,
f) if the selected cauliflower plant has a color score equal or greater than C4 on the Ctifl color chart, repeating steps b) through d) using the selected cauliflower plant in each successive round as the first parent until a cauliflower plant having a color score less than C4 on the Ctifl color chart has been produced.
thereby producing a cauliflower having a brilliant white curd.

Embodiment 110. The method of embodiment 109, wherein said one or more markers is capable of detecting a nucleic acid sequence that is present on a linkage group selected from the group consisting of linkage group 1, 2, 7, or 9 within 100 kb of said white curd allele.

Embodiment 111. The method of embodiment 110, wherein said nucleic acid molecule is capable of detecting a nucleic acid sequence that is present on a linkage group selected from the group consisting of linkage group 1, 2, 7, or 9 within 50 kb of said white curd allele.

Embodiment 112. The method of embodiment 111, wherein said nucleic acid molecule is capable of detecting a nucleic acid sequence that is present on a linkage group selected from the group consisting of linkage group 1, 2, 7, or 9 within 25 kb of said white curd allele.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 provides one embodiment of interval mapping plots for the brilliant white (BW) curd trait in cauliflower of linkage groups O1, O2, O7, and O9.

FIG. 2 provides one embodiment of interval mapping plots for the brilliant white curd trait in cauliflower of linkage group O9.

FIG. 3 provides one embodiment of interval mapping plots for the brilliant white curd trait in cauliflower of linkage group O1.

FIG. 4 provides one embodiment of an INDEL polymorphism between donor line NY6633 and recipient line ED37 for the white allele at marker QTLO7.

DETAILED DESCRIPTION OF THE INVENTION

Figure 5:
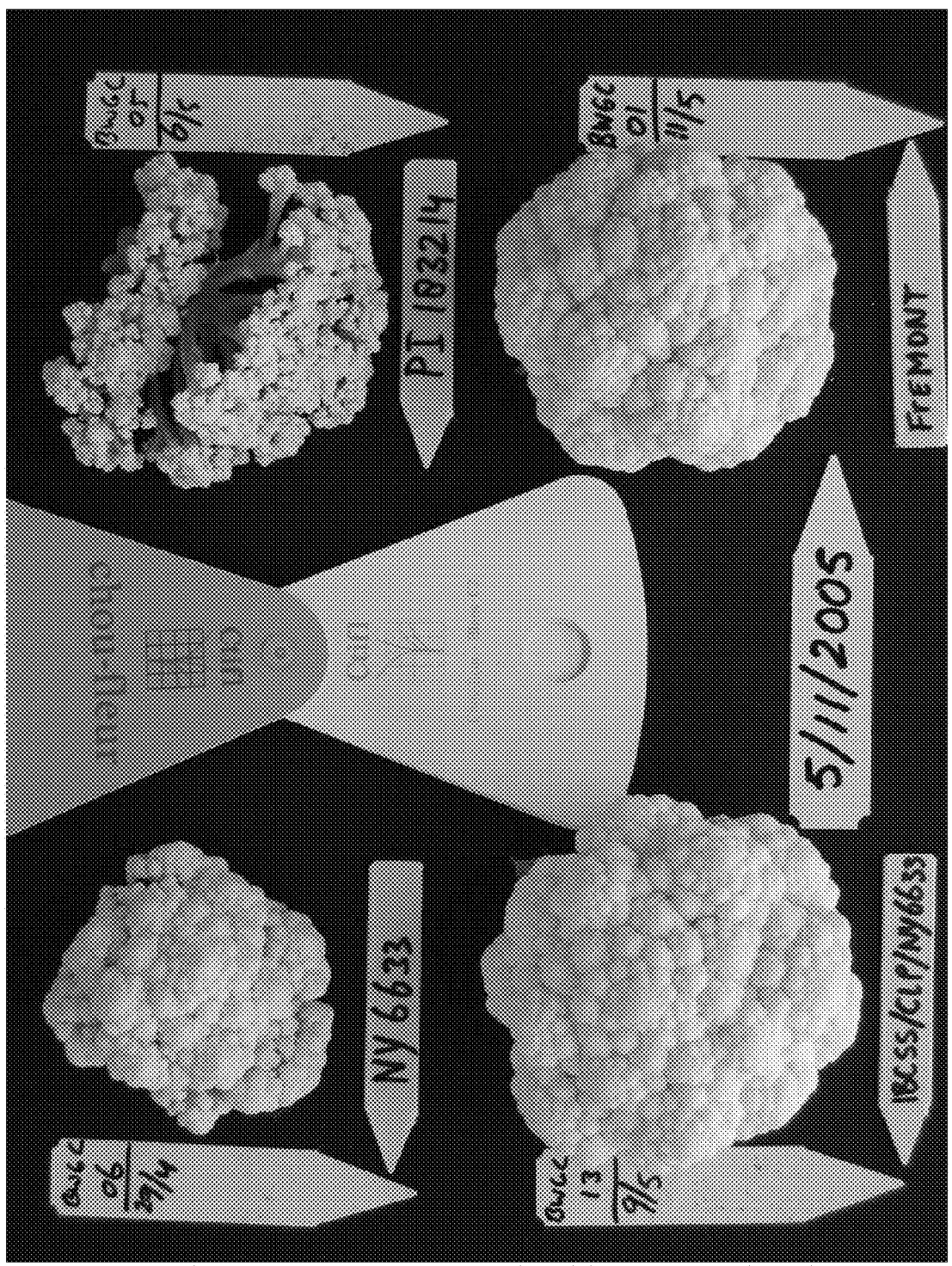
FIG. 5 is a photograph comparing elite brilliant white cauliflower lines to parental lines and one commercial hybrid (Fremont). The upper panel sets forth exemplary curds of the "BW source" parental lines NY6633 (left upper) and PI183214 (right upper). The lower panel sets forth exemplary curds of the elite brilliant white cauliflower lines IBCSS/CLP/NY6633 (left lower) and from the control hybrid, Fremont (right lower). As compared to the "BW source" parental lines NY6633 and PI183214, the curds of brilliant white elite lines are whiter in color, have larger curd size and superior curd quality.

This application discloses cauliflowers having a brilliant white curd. Such cauliflowers can be referred to as brilliant white cauliflower varieties. Methods of breeding brilliant white cauliflower lines are also provided. Also disclosed herein are quantitative trait loci associated with the brilliant white curd trait.

As used herein, a "brilliant white" cauliflower is any cauliflower with curds, grown uncovered, having an average color score of less than C4, for example a color score between C2 and C4, referred to herein as C3, on the Ctifl (Centre technique interprofessionnel des fruits et legumes, 22. Rue Bergere, 75009 Paris-France) cauliflower color chart (when measured under controlled light (TL) conditions or a combination of controlled and ambient light) as described in Example 7. Brilliant white cauliflower lines have a whiteness score that is lower than (i.e., is more white than) previously described cauliflower plants, such as, the BW source lines PI183214 and NY6633.

In another aspect, the present invention provides a cauliflower, when grown without cover, having an average curd color score of less than or equal to about C4 on a Ctifl cauliflower color chart. In one aspect, the cauliflower plants produce a curd having a curd color score of less than or equal to about C4 after growth without cover for a period of about 1, 2, 3, 4, 5, 6, 7, 8, 9, 10 days, 1, 2, 3, or 4 weeks. In a preferred aspect, the cauliflower plants produce a curd having a curd color score of less than or equal to about C4 after growth without cover for a period about 2 weeks.

Cauliflowers disclosed within also include those that can be referred to as persistent white cauliflowers. As used herein, "persistent white" cauliflower refers to cauliflower having a curd that does not discolor from white to creamy when exposed to sunlight and does therefore not require covering or tying in the field prior to harvest. A brilliant white cauliflower can be also a persistent white cauliflower and vice versa.

As used herein, a "control" cauliflower is a cauliflower selected from the group consisting of Fremont F1, Cornell F1, Aviso (Clause) F1, Aviron (Clause) F1, and Fortados OP. In a preferred aspect, Fremont F1 is the control cauliflower. A control cauliflower is also grown under similar environmental conditions as the test cauliflower.

As used herein, storage at "controlled coldstore" conditions means storage at about 4-8° C. As used herein, "ambient conditions" means shelf temperature, e.g., stored indoors at about 18-22° C. during the day and about 13-17° C. during the night.

As used herein, "linkage" is a phenomenon wherein alleles on the same chromosome tend to segregate together more often than expected by chance if their transmission was independent.

As used herein, a "marker" is an indicator for the presence of at least one phenotype, genotype, or polymorphism. Examples of DNA markers are single nucleotide polymorphisms (SNPs), cleaved amplified polymorphic sequences (CAPS), amplified fragment length polymorphisms (AFLPs), restriction fragment length polymorphisms (RFLPs), simple sequence repeats (SSRs), insertions or deletions (INDELs), or random amplified polymorphic DNA (RAPDs). A marker is preferably codominant (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism or phenotype.

In one aspect, cauliflower plants having a brilliant white curd contain one or more markers linked to a quantitative trait locus or loci (QTL) controlling the brilliant white trait. In a preferred aspect, the cauliflowers contain one or more markers linked to a QTL on linkage group O1, O2, O7, or O9. In another preferred aspect, the cauliflowers contain one or more markers selected from the group of QTLO1, QTLO2a, QTLO2b, QTLO7, and QTLO9. In a more preferred aspect, the cauliflower plants have one or more markers that hybridize to SEQ ID NOs: 1, 6, 11, 14, or 17.

As used herein, two nucleic acid molecules are said to be capable of hybridizing to one another if the two molecules are capable of forming an anti-parallel, double-stranded nucleic acid structure. Conventional stringency conditions are described by Sambrook et al., *Molecular Cloning*, A Laboratory Manual, *2nd Ed.*, Cold Spring Harbor Press, Cold Spring Harbor, New York (1989) and by Haymes et al., *Nucleic Acid Hybridization, A Practical Approach*, IRL Press, Washington, DC (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. In one aspect, hybridization conditions can be high, moderate or low stringency conditions. Preferred conditions include those using 50% formamide, 5.0×SSC, 1% SDS and incubation at 42° C. for 14 hours, followed by a wash using 0.2×SSC, 1% SDS and incubation at 65° C.

In one aspect, specificity of hybridization can be affected by post-hybridization washes. For example, the salt concentration in the wash step can be selected from a low stringency of about 2.0×SSC at 50° C. to moderate stringency of about 1.0×SSC at 50° C. to a high stringency of about 0.2×SSC at 50° C. In addition, the temperature in the wash step can be increased from low stringency conditions at room temperature, about 22° C., to moderate stringency conditions at about 50° C., to high stringency conditions at about 65° C. Both temperature and salt may be varied, or either the temperature or the salt concentration may be held constant while the other variable is changed. In one aspect, the wash step can be performed for 5, 10, 15, 20, 25, 30, or more minutes. In a preferred aspect, the wash step is performed for about 20 minutes. In another aspect, the wash step can be repeated 1, 2, 3, 4, or more times using the selected salt concentration, temperature, and time. In a preferred aspect, the wash step is repeated twice.

In a preferred aspect, a nucleic acid of the present invention will specifically hybridize to one or more of the nucleic acid markers of SEQ ID NOs, 1, 6, 11, 14, or 17 or complements thereof under moderately stringent conditions, for example at about 2.0×SSC and about 65° C.

In another aspect, the present invention provides a cauliflower plant having at least four brilliant white alleles. In a preferred aspect, the cauliflower plant has at least two, three, four, or all five, brilliant white alleles selected from the group of QTLO1, QTLO2a, QTLO2b, QTLO7, and QTLO9. In a more preferred aspect, the cauliflower plant also produces a brilliant white curd.

The present application provides for cauliflower plants having favorable curd characteristics. Cauliflower is sensitive to unfavorable climate conditions. Unusually hot or cold weather, and drought, can result in curds of poor quality in the earlier season types. The growing conditions for cauliflower are fairly exacting, requiring rich soil and favorable climatic conditions, e.g., a comparatively cool temperature with a moist atmosphere. For this reason commercial cauliflower production naturally tends toward higher altitude regions though it can be grown successfully at lower altitudes if it is planted to mature before summer or, alternatively, for harvest in the late fall. Curd initiation is temperature dependent, with hot temperatures delaying curd initiation, though varieties also differ in the time required to produce harvestable curds after initiation has occurred. The combination of time required for the juvenile phase, the mature vegetative phase, the time needed to produce a marketable curd after induction, and the response of a variety to temperature at all these stages, determine the suitability and adaptability of a given variety.

Certain curd quality traits are particularly important to the commercial value of the crop, and the lack of these other quality traits can equally adversely affect the market for the cauliflower. For example, "bracting" occurs under warm growing conditions, and results from growth of small, white or green leaves through the curd. "Fuzzyness" is the result of early flower bud primordia growing out of the curd, and is also induced at elevated temperature. A review of these traits is found in "Comparing Genetic And Physical Organisation Of Gene Families Affecting Plant Development Within *Brassica* And *Arabidopsis*", King. G. J., et al., 10th International Rapeseed Congress, Canberra 1999. Bracting, and fuzzyness can be measured by any method known in the art. For example, bracting, and hairyness may be measured by comparison of a test curd to a control cauliflower curd grown under similar conditions. In another aspect, cauliflower plants described herein are essentially free or free of bracting. In an aspect, the test curd has an amount of bracting that is less than 10%, 20%, 30%, 40%, 50%, 60%, 70%, 80%, or 90% a standard cauliflower curd grown under similar conditions. In another aspect, brilliant white cauliflower plants described herein are essentially free or free of hairyness. In yet another aspect, the test curd has an amount of hairyness that is less than 10%, 20%, 30%, 40%, 50%, 60%, 70%, 80%, or 90% a standard cauliflower curd grown under similar conditions.

In an aspect, a cauliflower has a curd diameter at harvest of about or greater than 13.0 centimeters (cm), 13.1 cm, 13.2 cm, 13.3 cm, 13.4 cm, 13.5 cm, 13.6 cm, 13.7 cm, 13.8 cm, 13.9 cm, 14.0 cm, 14.1 cm, 14.2 cm, 14.3 cm, 14.4 cm, 14.5 cm, 14.6 cm, 14.7 cm, 14.8 cm, 14.9 cm, 15.0 cm, 15.1 cm, 15.2 cm, 15.3 cm, 15.4 cm, 15.5 cm, 15.6 cm, 15.7 cm, 15.8 cm, 15.9 cm, 16.0 cm, 16.1 cm, 16.2 cm, 16.3 cm, 16.4 cm, 16.5 cm, 16.6 cm, 16.7 cm, 16.8 cm, 16.9 cm, or 17.0 cm. As used herein, curd diameter at harvest is measured by measuring the diameter of the two points of greatest distance on the curd.

In an aspect, a cauliflower has a curd weight (i.e., weight of curd with no leaves attached or 'naked' curd at harvest) of about or greater than 350 grams, 360 grams, 380 grams, 400 grams, 420 grams, 440 grams, 460 grams, 480 grams, 500 grams, 520 grams, 540 grams, 550 grams, 560 grams, 580 grams, 600 grams, 620 grams, 640 grams, 650 grams, 660 grams, 680 grams, 700 grams, 720 grams, 740 grams, 750 grams, 760 grams, 780 grams, 800 grams, 820 grams, 840 grams, 850 grams, 5860 grams, 880 grams, 900 grams, 920 grams, 940 grams, 950 grams, 960 grams, 980 grams, or 1000 grams. As used herein, weight of 'naked' curd at harvest is measured by weighing the harvested curd on a scale.

In an aspect, a cauliflower has a curd depth at harvest of about or greater than 80 millimeters (mm), 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, 101 mm, 102 mm, 103 mm, 104 mm, 105 mm, 106 mm, 107 mm, 108 mm, 109 mm, 110 mm, 111 mm, 112 mm, 113 mm, 114 mm, 115 mm, 116 mm, 117 mm, 118 mm, 119 mm, or 120 mm. Curd depth is measured at the curd height from top to bottom in millimeters. As used herein, curd depth is measured by measuring the distance between the top and the bottom of the harvested "naked" curd.

In an aspect, a cauliflower has a "jacket", or percentage of curd bottom covered, at the time of harvest of about or greater than 85%, 86%, 87%, 88%, 89%, 90%, 91%, 92%, 93%, 94%, 95%, 96%, 97%, 98%, 99%, or 100%. "Jacket", or percentage of curd bottom covered, at the time of harvest is measured by subtracting the area of the curd bottom covered from the total area of the curd bottom, dividing by the total area of the curd bottom and multiplying by 100.

In an aspect, a cauliflower has a "self-covering", or percentage of curd top covered of about or greater than 15%, 16%, 18%, 20%, 22%, 24%, 25%, 26%, 28%, 30%, 32%, 34%, 35%, 36%, 38%, 40%, 42%, 44%, 45%, 46%, 48%, 50%, 62%, 64%, 65%, 66%, 68%, or 70%. "Self-covering", or percentage of curd top covered is measured by subtracting the area of the curd top covered from the total area of the curd top, dividing by the total area of the curd top and multiplying by 100.

In an aspect, a cauliflower has a overall curd quality rating of 1, 2, 3, 4, or 5, where curd quality is measured by visual inspection, with a scale ranging from 1=poor through 5=excellent. In a preferred aspect, the overall curd quality is measured as a General Impression ("GI") score, with a scale ranging from 1=poor through 5=excellent. In one aspect, the GI score combines measurements from many curd quality factors including jacket, covering, curd shape, curd depth, curd weight, bead, structure, riciness, bracting, and fuzzyness.

In one aspect, the present invention provides a cauliflower curd having an average curd color score of less than about C4 on a Ctifl cauliflower color chart, when grown without cover, and having a GI score of greater than 3. In a preferred aspect, the GI score is greater than 4.

In an aspect, during storage under ambient conditions a cauliflower exhibits a change in color relative to the color score on the Ctifl color chart measured at harvest of less than or about 5%, 10%, 15%, 20%, 25%, 30%, 35%, 40%, 45%, 50%, 55%, 60%, 65%, 70%, 75%, 80%, 85%, 90% or 95%. In another aspect, during storage at 5° C. a cauliflower exhibits a change in color relative to the color score on the Ctifl color chart measured at harvest of less than or about 5%, 10%, 15%, 20%, 25%, 30%, 35%, 40%, 45%, 50%, 55%, 60%, 65%, 70%, 75%, 80%, 85%, 90% or 95%. Color score on the Ctifl color chart is measured as described in Example 7.

In an aspect, during storage at 5° C. a cauliflower exhibits a change in curd weight relative to curd weight measured at harvest of less than 5%, less than 10%, less than 15%, less than 20%, less than 25%. In another aspect, during storage at ambient conditions a cauliflower exhibits a change in curd weight relative to curd weight measured at harvest of less than 5%, less than 10%, less than 15%, less than 20%, less than 25%. In another aspect, during storage at ambient conditions a cauliflower exhibits a change in curd weight relative to curd weight measured at harvest of 5%, 10%, 15%, 20%, 25%, 30%, 35%, 40%, 45%, 50%, 55%, 60%, 65%, 70%, 75%, 80%, 85%, 90% or 95%. In yet another aspect, during storage at 5° C. a cauliflower exhibits a change in curd weight relative to curd weight measured at harvest of 5%, 10%, 15%, 20%, 25%, 30%, 35%, 40%, 45%, 50%, 55%, 60%, 65%, 70%, 75%, 80%, 85%, 90% or 95%.

A cauliflower attribute such as color, curd weight, curd diameter and depth, riciness, hairiness, or jacket percentage can be measured at a variety of times. In another aspect, an attribute is measured following growth in a growth chamber. In another aspect, an attribute is measured following growth in a field. In one aspect, an attribute is measured at the time of harvest. In another aspect, an attribute is measured after storage of the cauliflower at ambient conditions for one day, two days, three days, four days, five days, six days, one week, or two weeks after harvest. In yet another aspect, an attribute is measured after storage of the cauliflower at 5° C. for one day, two days, three days, four days, five days, six days, one week, two weeks, or three weeks.

As used herein, a cauliflower plant exhibits "favorable curd characteristics" if the curd has a diameter of about 15 centimeters and a weight of at least 700 grams, and has a minimal amount of bracting, riciness, and fuzzyness. In a preferred aspect, the curd shows no bracting, riciness, and fuzzyness. As used herein, a "minimal amount of bracting, riciness, and fuzzyness," refers to a curd having an intermediate amount of bracting, riciness, or fuzzyness compared to a standard cauliflower line. Bracting, riciness and fuzzyness can be measured using any method available for measuring such traits. For example, fuzzyness can be measured using a scale of 1 to 5: 1 being absent, 3 being intermediate fuzzyness, and 5 being completely fuzzy.

A further aspect of the invention relates to tissue cultures of the cauliflower lines described herein. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryo, leaf, peduncle, pedicel, anther, meristem, tip and segments of root, stump and stem, curd explants, and the like. In a preferred aspect, the tissue culture comprises embryos, protoplasts, meristematic cells, pollen, leaves or anthers derived from immature tissues of these plant parts. Means for preparing and maintaining plant tissue cultures are well known in the art. Examples of processes of tissue culturing and regeneration of cauliflower are described in, for example, Keiffer et al, ISHS Symposium on Brassicas, Ninth Crucifer Genetics Workshop (1994); and Ross, C. L., Tissue Culture Methods for Plant Pathologist (1980).

The present invention also provides a seed of a cauliflower plant in which curds obtained from cauliflower plants grown for the seed have a brilliant white trait. In one aspect, the present invention provides a seed of a cauliflower plant in which a plant grown from the seed is male sterile. In one aspect, the present invention provides seed of cauliflower variety CLP/NY6633/9/FRE (representative sample of seed having been deposited under NCIMB Accession No. 41432). In another aspect, the present invention provides seed of a cauliflower variety CLP/NY6633 (representative sample of seed having been deposited under NCIMB Accession No. 41430). In yet another aspect, the present invention provides seed of a cauliflower variety BCSS/CLP/NY6633 (representative sample of seed having been deposited under NCIMB Accession No. 41431). In another aspect, the present invention provides seed of a cauliflower variety CLP/NY6633/9/FRE/CLP/NY6633/HOCE (representative sample of seed having been deposited under NCIMB Accession No. 41433).

In another aspect, the present invention also provides for a plant grown from the seed of a cauliflower plant in which curds obtained from cauliflower plants grown for the seed have a brilliant white trait, as well as plant parts and tissue cultures from such plants.

The present invention also provides a container of cauliflower seeds in which curds obtained from cauliflower plants grown from greater than 50% of the seeds have a brilliant white trait. In another aspect, curds obtained from cauliflower plants grown from greater than 55%, 60%, 65%, 70%, 75%, 80%, 85%, 90%, 95% of the cauliflower seeds in the container have a brilliant white trait.

The container of cauliflower seeds may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10, ounces, 1 pound, 2 pounds, 3 pounds, 4 pounds, 5 pounds or more seeds.

Containers of cauliflower seeds may be any container available in the art. By way of non-limiting example, a container may be a box, a bag, a packet, a pouch, a tape roll, a pail, a foil, or a tube.

In another aspect, the present invention also provides a container of cauliflower curds in which greater than 50% of the curds have a brilliant white trait. In another aspect, greater than 55%, 60%, 65%, 70%, 75%, 80%, 85%, 90%, 95% of the curds in the container have a brilliant white trait.

The container of curds may contain any number, weight or volume of curds. For example, a container can contain at least, or greater than, about 5, 10, 15, 20, 25, 30, 35, 40, 45, 50, or 100 curds. Alternatively, the container can contain at least, or greater than, about 1 pound, 2 pounds, 3 pounds, 4 pounds, 5 pounds or more curds.

Containers of curds may be any container available in the art. By way of non-limiting example, a container may be a box, a flat, a bag, a packet, or a bunch. A container of curds of the present invention may be found in any location, including, but not limited to a warehouse, a distributor, a wholesaler, or a retail market, such as a grocery store.

In another aspect, the present invention provides a cauliflower plant having a genome, in which comprises a genetic locus derived from a brilliant white cauliflower plant. In a preferred aspect, the brilliant white cauliflower is selected from the group consisting of CEL/1857, PI183214, 901203-2/FREMONT, NY6633, NY3339, 90331, BCSS, HOCE, and PWCE. In one aspect, the genetic locus derived from a brilliant white cauliflower can be identified using genetic markers. In a preferred aspect, the genetic locus contains one, two, three, four, or five alleles of a quantitative trait locus genetically linked to the complement of a marker nucleic acid molecule selected from the group consisting of QTLO1, QTLO2a, QTLO2b, QTLO7, and QTLO9.

In one aspect, any amount a cauliflower plant genome can be derived from a brilliant white cauliflower. In a preferred aspect, a cauliflower plant can have 50%, 25%, 12.5% or less genetic material derived from a brilliant white cauliflower plant.

In one aspect, a cauliflower plant can contain any number of brilliant white quantitative trait loci. In a preferred aspect, a cauliflower plant contains at least 1, 2, 3, 4, 5, 6, 7, 8, 9, or 10 alleles associated with brilliant white quantitative trait loci. In another aspect, a cauliflower has a genome have 1 or more, 2 or more, 3 or more, 4 or more, or all 5 of a nucleic acid marker selected from the group of QTLO1, QTLO7, QTLO2a, QTLO2b, or QTLO9. In another aspect, a cauliflower plant can contain any combination of alleles associated with the quantitative trait loci.

Any appropriate method may be used to screen for a plant having a "brilliant white" allele at a quantitative trait locus related to the brilliant white trait, such as, one or more of QTLO1, QTLO7, QTLO2a, QTLO2b, or QTLO9. In a preferred aspect, a nucleic acid marker of the present invention can be used.

As used herein linkage of a nucleic acid sequence with another nucleic acid sequence may be genetic or physical. In a preferred aspect, a nucleic acid marker is genetically linked to QTLO1, QTLO7, QTLO2a, QTLO2b, or QTLO9, where a genotype identified by a marker exhibits a LOD score of greater than 2.0, as judged by interval mapping, for the brilliant white trait, preferably where the marker genotype exhibits a LOD score of greater than 3.0, as judged by interval mapping, for the brilliant white trait, more preferably where the marker genotype exhibits a LOD score of greater than 3.5, as judged by interval mapping, for the brilliant white trait and even more preferably where the marker nucleic acid molecule exhibits a LOD score of about 4.0, as judged by interval mapping, for the brilliant white trait based on maximum likelihood methods described by Lander and Botstein, Genetics, 121:185-199 (1989), and implemented, for example in the software package MAPMAKER/QTL (default parameters)(Lincoln and Lander, Mapping Genes Controlling Quantitative Traits Using MAPMAKER/QTL, Whitehead Institute for Biomedical Research, Massachusetts, (1990)).

In another aspect, the nucleic acid marker is genetically linked between about 0 and about 50 centimorgans (cM) to QTLO1, QTLO7, QTLO2a, QTLO2b, or QTLO9, more preferably, between about 0 and about 40 cM, between about 0 and about 25 cM, between about 0 and about 10 cM, between about 0 and about 5 cM, or between about 0 and about 3 cM In another aspect the nucleic acid molecule may be physically linked to QTLO1, QTLO7, QTLO2a, QTLO2b, or QTLO9. In a preferred aspect, the nucleic acid marker specifically hybridizes to a nucleic acid molecule having a sequence that is present on linkage group O1, O7, O2, or O9 within 500 kb or 100 kb, more preferably within 50 kb, even more preferably within 25 kb of QTLO1, QTLO7, QTLO2a, QTLO2b, or QTLO9. In a preferred aspect the nucleic acid marker is capable of specifically hybridizing to a nucleic acid molecule having a sequence that is present on linkage group O1, O7, O2, or O9 within 500 kb or 100 kb, more preferably within 50 kb, even more preferably within 25 kb of QTLO1, QTLO7, QTLO2a, QTLO2b, or QTLO9.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data is disclosed in U.S. Pat. No. 5,492,547, the disclosure of which is specifically incorporated herein by reference in its entirety. Such predictions may be made using any suitable genetic marker, for example, SSRs, CAPS, INDELs, RFLPs, AFLPs, SNPs, or isozymes.

In a preferred aspect of the present invention, a nucleic acid marker is selected from the group of nucleic acid markers of SEQ ID NO: 1, 6, 11, 14, 17, complements thereof, and fragments thereof.

Additional markers, such as SSRs, AFLP markers, RFLP markers, RAPD markers, phenotypic markers, SNPs, isozyme markers, microarray transcription profiles that are genetically linked to or correlated with alleles of a QTL of the present invention can be utilized (Walton, *Seed World* 22-29 (July, 1993); Burow and Blake, *Molecular Dissection of Complex Traits*, 13-29, Eds. Paterson, CRC Press, New York (1988)). Methods to isolate such markers are known in the art. For example, locus-specific SSRs can be obtained by screening a genomic library for SSRs, sequencing of "positive" clones, designing primers which flank the repeats, and amplifying genomic DNA with these primers.

The genetic linkage of marker molecules can be established by a gene mapping model such as, without limitation, the flanking marker model reported by Lander and Botstein, Genetics, 121:185-199 (1989), and the interval mapping, based on maximum likelihood methods described by Lander and Botstein, Genetics, 121:185-199 (1989), and implemented in the software package MAPMAKER/QTL (Lincoln and Lander, Mapping Genes Controlling Quantitative Traits Using MAPMAKER/QTL, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.), JoinMap (Kyazma B. V., Wageningen, Netherlands), and mapQTL (Kyazma B. V., Wageningen, Netherlands).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL (MLE given no linked QTL).

The LOD score indicates how much more likely the data are to have arisen assuming the presence of a QTL allele than in its absence. The LOD threshold value for avoiding a false positive with a given confidence, say 95%, depends on the number of markers and the length of the genome. Graphs indicating LOD thresholds are set forth in Lander and Botstein, Genetics, 121:185-199 (1989), and further described by Ars and Moreno-Gonzlez, Plant Breeding. Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, Genetics, 139:1421-1428 (1995)). Multiple regression methods or models can be also be used, in which the trait is regressed on a large number of markers (Jansen, Biometrics in Plant Breed, van Oijen, Jansen (eds.) Proceedings of the Ninth Meeting of the Eucarpia Section Biometrics in Plant Breeding. The Netherlands, pp. 116-124 (1994); Weber and Wricke, Advances in Plant Breeding, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, Genetics, 136:1447-1455 (1994) and Zeng, Genetics, 136:1457-1468 (1994). Generally, the use of cofactors reduces the bias and sampling error of the estimated QTL positions (Utz and Melchinger, Biometrics in Plant Breeding, van Oijen, Jansen (eds.) Proceedings of the Ninth Meeting of the Eucarpia Section Biometrics in Plant Breeding. The Netherlands, pp. 195-204 (1994), thereby improving the precision and efficiency of QTL mapping (Zeng, Genetics, 136:1457-1468 (1994)). These models can be extended to multi-environment experiments to analyze genotype-environment interactions (Jansen et al., Theo. Appl. Genet. 91:33-37 (1995)).

Using a LOD score of 2.5 as a significance level, whiteness in cauliflower was determined to be governed by at least five QTL. One QTL was found on linkage groups O1, O7 and O9, and two QTL were found on linkage group O2. An epistatic interaction was found between the QTL on linkage groups O1 and O9.

Selection of an appropriate mapping or segregation populations is important to map construction. The choice of appropriate mapping population depends on the type of marker systems employed (Tanksley et al., Molecular mapping plant chromosomes. Chromosome structure and function: Impact of new concepts J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less genetic material derived from one of the two originally crossed plants. As used herein, a second plant is derived from a first plant if the second plant's pedigree includes the first plant.

An $F_2$ population is the first generation of self or sib pollination after the hybrid seed is produced. Usually a single $F_1$ plant is self- or sib-pollinated to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g., $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g., disease resistance) or where trait expression is controlled by a QTL. Segregation data from progeny test populations (e.g., $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about ≤10% recombination), dominant and co-dominant markers evaluated in RIL populations provide more information per individual than either marker type in backcross populations (Reiter et al., Proc. Natl. Acad. Sci. (U.S.A) 89:1477-1481 (1992)). However, as the distance between markers becomes larger (i.e., loci become more independent), the information in RIL populations decreases dramatically when compared to codominant markers.

Backcross populations can be utilized as a mapping population. A backcross population is created by one or more crosses from an F1 with one of the parentals. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., Proc. Natl. Acad. Sci. (U.S.A) 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the genetic distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore, et al., Proc. Natl. Acad. Sci. (U.S.A) 88:9828-9832 (1991)). In BSA, two bulked DNA samples are created from a segregating population originating from a single cross. These bulks contain individuals that are identical for a particular trait (for example, resistant or sensitive to particular disease) or genomic region. For unlinked or distantly (~50 cM) linked loci, the frequency of alleles reflect that predicted by independent assortment and the population structure. Regions unlinked to the target region will not differ between the BSA bulked samples.

The present application provides a genetic complement of the cauliflower lines described herein (e.g., F7 CLP/ NY6633, F5 CLP/NY6633/9/FRE, F4 BCSS/CLP/NY6633, and F4 CLP/NY6633/9/FRE/CLP/NY6633/HOCE). Further provided is a hybrid genetic complement, where the complement is formed by the combination of a haploid genetic complement from elite inbred cauliflower lines described herein and another haploid genetic complement. Means for determining such a genetic complement are well-known in the art.

As used herein, the phrase "genetic complement" means an aggregate of nucleotide sequences, the expression of which defines the phenotype of a cauliflower plant or a cell or tissue of that plant. By way of example, a cauliflower plant is genotyped to determine a representative sample of the inherited markers it possesses. Markers identify alleles at a single locus. Markers are preferably codominant so they can discern both homozygote and heterozygote genotypes. Thus, the allelic composition at a diploid locus is readily detectable irrespective of any environmental variation. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

In another aspect, the present invention provides a method of introgressing at least one brilliant white curd allele into a cauliflower plant, comprising crossing a plant from a first cauliflower line as a first parent having at least one brilliant white curd allele with a second cauliflower plant as a second parent to form a segregating population, screening the segregating population for a member having at least one white curd allele with a nucleic acid molecule capable of identifying a white allele at QTLO1, QTLO2a, QTLO2b, QTLO7, or QTLO9, and selecting a cauliflower plant that contains at least one white allele at QTLO1, QTLO2a, QTLO2b, QTLO7, or QTLO9 for further crossing.

In another aspect, the present invention provides a method of producing a cauliflower having a brilliant white curd comprising
a) selecting a plant from cauliflower line CEL/1857 as a first parent
b) crossing the first parent with a second cauliflower plant from a cauliflower line selected from the group consisting of CEL/1857, PI183214, 901203-2/FREMONT, NY6633, NY3339, 90331, BCSS, HOCE, and PWCE as a second parent,
c) growing cauliflower seed produced by the cross to yield a progeny cauliflower plant,
d) determining a color score on the Ctifl color chart for the progeny cauliflower plant,
e) if the progeny cauliflower plant has a color score of equal or greater than C4 on the Ctifl color chart, repeating steps b) through d) using the progeny cauliflower plant in each successive round as the first parent until a cauliflower plant having a color score less than C4 on the Ctifl color chart has been produced, thereby producing a cauliflower having a brilliant white curd.

In still another aspect, the present invention provides a method of producing a cauliflower having a brilliant white curd comprising
a) selecting a plant from a cauliflower line selected from the group consisting of CEL/1857, PI183214, 901203-2/FREMONT, NY6633, NY3339, 90331, BCSS, HOCE, and PWCE as a first parent
b) crossing the first parent with a second cauliflower plant selected from the group consisting of CEL/1857, PI183214, 901203-2/FREMONT, NY6633, NY3339, 90331, BCSS, HOCE, and PWCE as a second parent to form a segregating population,
c) screening the segregating population with one or more nucleic acid markers capable of detecting a brilliant white allele at QTLO1, QTLO2a, QTLO2b, QTLO7, and QTLO9;
d) selecting from the segregating population a cauliflower plant that is homozygous for a brilliant white allele at QTLO1, QTLO2a, QTLO2b, QTLO7, and QTLO9,
e) determining a color score on the Ctifl color chart for the selected cauliflower plant,
f) if the selected cauliflower plant has a color score of equal or greater than C4 on the Ctifl color chart, repeating steps b) through d) using the selected cauliflower plant in each successive round as the first parent until a cauliflower plant having a color score less than C4 on the Ctifl color chart has been produced, thereby producing a cauliflower having a brilliant white curd.

The present invention also provides for parts of the cauliflower plants produced by a method of the present invention. Plant parts, without limitation, include seed, endosperm, ovule and pollen. In a particularly preferred embodiment of the present invention, the plant part is a seed.

Plants generated using a method of the present invention can be part of or generated from a breeding program. The choice of breeding method depends on the mode of plant reproduction, the heritability of the trait(s) being improved, and the type of cultivar used commercially (e.g., $F_1$ hybrid cultivar, pure line cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, curd size, seed set, and seed density will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new cauliflower lines requires the development and selection of cauliflower varieties, the crossing of these varieties and selection of superior hybrid crosses. The hybrid seed can be produced by manual crosses between selected male-fertile parents or by using male sterility systems. Hybrids are selected for certain single gene traits such as flower color, seed yield, or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to deriving a new generation from a single seed from the previous generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (e.g., Fehr, *Principles of Cultivar Development* Vol. 1, pp. 2-3 (1987)).

The present invention provides a method of introgressing a brilliant white curd allele into a cauliflower plant comprising: performing marker assisted selection of the cauliflower plant with a nucleic acid marker, where the nucleic acid marker specifically hybridizes with a nucleic acid molecule having a first nucleic acid sequence that is physically linked to a second nucleic acid sequence that is located on linkage group O1, O2, O7, or O9, where the second nucleic acid sequence is within 500 kb of a third nucleic acid sequence which is capable of specifically hybridizing with the nucleic acid sequence of SEQ ID NO: 1, 6, 11, 14, or 17, complements thereof, or fragments thereof; and, selecting the cauliflower plant based on the marker assisted selection.

In a preferred aspect of the present invention the source of one or more white curd alleles for use in a breeding program is derived from a plant selected from the group consisting of Celesta, Linas, Fremont, Balboa, Belot, Jerez, Sevilla, Skywalker, Aviron, Beluga, Defino, Meridien, Moby Dick, Nessie, Rafale, Redoubtable, Elinia, Valtos, Veronie, Viviane, Deniol, Hef, Juluan, Miliau, Nelig, Nevis, Nominoe, Ceveline, Opaal, Chambord, Abruzzi, Albino, Amiata, Armstrong, Baldo, Cadal, Conero, Cornell, Freedom, Hermon, Lattai, Premato, Sasso, Sublime, Vinson, Vulture, Baker, Boulen, Broden, Clapton, Celemen, Diamen, Lecanu, Lorien, PI183214, NY6633, and Magellan. In a more preferred aspect, the source of the brilliant white curd alleles for use in a breeding program is derived from a plant selected from the group consisting of PI183214 and NY6633.

In light of the current disclosure, plant introductions and germplasm can be screened with a marker nucleic acid molecule of the present invention to screen for alleles of the white curd trait using one or more of techniques disclosed herein or known in the art.

Every reference, patent, or other published work cited above is herein incorporated by reference in its entirety.

EXAMPLES

Example 1. Development of Cauliflower Line CLP/NY6633×9/FRE

The origin and breeding history of elite cauliflower line $F_5$ CLP/NY6633×9/FRE (=$F_5$ CEL/1857/PI183214/NY6633/901203/FREMONT) is summarized below. These cauliflower lines show uniformity and stability within the limits of environmental influence for the brilliant white trait.

An F3 CEL/1657 line (open pollinator ("O.P.") CELESTA (from Rijk Zwaan) cross with O.P. LINAS line (from Royal Sluis) is crossed with cauliflower line PI183214 to produce the $F_1$ line CEL/1857/PI183214. The $F_1$ line is self-crossed to produce an $F_2$ line. The $F_2$ line is crossed with an $F_5$ CEL/1657 line to produce backcross line 1 ($BC_1$) CEL/1857/PI183214, which is used in a backcross with an $F_6$ CEL/1657 line. This backcross resulted in $BC_3$ CEL/1857/PI183214 line. A $BC_3Z_1$ CEL/1857/PI183214 is then crossed with a $F_N$ NY6633 line to produce $F_1$ CEL/1857/PI183214/NY6633, which, through multiple self-crosses, yielded an F3 CEL/1857/PI183214/NY6633 line. The $F_3$ CEL/1857/PI183214/NY6633 line is crossed with an $F_3$ 901203/Fremont line to produce an $F_1$ CEL/1857/PI183214/NY6633/901203/Fremont line. This line is line self-crossed through multiple self-crosses to produce an $F_5$ CEL/1857/PI183214/NY6633/901203/Fremont line.

The $F_3$ 901203/Fremont line is developed by crossing an $F_N$ 901203 line with an $F_1$ Fremont line to yield an $F_1$ 901203/Fremont line, which is self-crossed to produce an $F_3$ line.

Example 2. Development of Cauliflower Line CLP/NY6633

The origin and breeding history of elite cauliflower line CLP/NY6633 (An F7 CEL/1857/PI83214/NY6633 line) is summarized below. These cauliflower lines show uniformity and stability within the limits of environmental influence for the brilliant white trait.

An $F_3$ CEL/1857 line (a result of crossing an O.P. CELESTA line (from Rijk Zwaan) with an O.P. Linas (line 1857 from Royal Sluis)) is crossed with an $F_N$ PI183214 line to produce the $F_1$ line CEL/1857/PI183214. An $F_2$ line is produced and crossed with an $F_5$ CEL/1857 line to produce a $BC_1$ CEL/1857/PI183214 line which in turn is backcrossed with an $F_6$ CEL/1857 line to yield a $BC_3$ CEL/1857/PI183214 line. The $BC_3Z_1$ CEL/1857/PI183214 line is crossed with an $F_N$ NY6633 line to produce an $F_1$ CEL/1857/PI183214/NY6633 line, which is self-crossed to produce an $F_7$ CEL/1857/PI183214/NY6633 line (CLP/NY6633).

Example 3. Development of Cauliflower Line IBCSS/CLP/NY6633

The origin and breeding history of elite cauliflower line IBCSS/CLP/NY6633 is summarized below. These cauliflower lines show uniformity and stability within the limits of environmental influence for the brilliant white trait.

An $F_3$ CEL/1857/PI183214/NY6633 line (described above) is crossed with an $FnZ_1$ BCSS (obtained from crossing a persistent white source, such as NY6633 or NY7642B with O.P variety Silverstar) to produce an $F_1$ 1BCSS/CEL/1857/PI183214/NY6633line which is self-crossed through multiple generations to yield an $F_4$ line (1BCSS/CLP/NY6633).

Example 4. Development of Cauliflower Line CLP/NY663×9/FRE/CLP/NY663/HOCE

The origin and breeding history of elite cauliflower line CLP/NY6633×9/FRE/CLP/NY6633/HOCE is summarized below. These cauliflower lines show uniformity and stability within the limits of environmental influence for the brilliant white trait.

An $F_2$ CEL/1857/PI183214/NY6633 line (as described above) is crossed with an $F_2$ 901203/Fremont line (resulting from a cross between an $F_N$ 901203 line with an $F_1$ Fremont line) to produce an $F_1$ 901203/Fremont/CEL/1857/PI183214/NY6633 line, which is crossed with an Fn PWHOCE line (obtained from crossing a persistent white source, such as NY6633 or NY7642B, with an HOCE line (derived from a cross between O.P. variety Hormade and Celesta)) to produce an $F_1$ 901203/Fremont/CEL/1857/PI183214/NY6633/HO/CE line. An $F_2$ 901203/Fremont/CEL/1857/PI183214/NY6633/HO/CE line is crossed with an $F_4$ CEL/1857/PI183214/NY663 line to yield an $F_1$ CEL/1857/PI183214/NY6633/901203/Fremont/CEL/1857/PI183214/NY6633/HO/CE line which is self-crossed to produce an $F_4$ line (CLP/NY6633×9/FRE/CLP/NY6633/HOCE).

Example 5. Cauliflower Field Trials

Cauliflower seeds are initially planted in a greenhouse. After about 7 weeks of growth, seedlings are transplanted to a field, at a spacing of 75×50 centimeters. Plants are grown in clay soil. The self-covering inner leaves are not removed. Curd color is evaluated as described in Example 7 using 3 replications, 5 heads/plot (datapoints are derived from 15 plants).

Development of color and weight after harvest at controlled conditions (5° C.) is analyzed in 3 cycles with measurements every 7 days, with the latest cycle measured at 21 days after harvest. One head is measured per plot.

Development of color and weight after harvest at ambient conditions (storage indoors, about 20° ° C. daytime, and 15° C. nighttime) is analyzed in 2 cycles with measurements every 7 days, with the latest cycle measured at 14 days after harvest. Four heads are measured per plot.

Field Trial data is shown in Table 1. The Marker profile data is represented as white (W), yellow (Y), segregating (S), and heterozygous (H). The diameter is represented as the measurement of the curd at harvest in centimeters (cm). The "jacket" refers to the percentage of the curd bottom covered, while "self covering" refers to the percent of the curd top covered. The weight of the curd is represented in grams of 'naked' curd and the depth represents the curd height from top to bottom in centimeters (cm). The "fuzzyness" score indicates that fuzzyness is absent ("1"), minimal fuzzyness ("2"), intermediate fuzzyness ("3"), substantial fuzzyness ("4"), or complete fuzzyness ("5"). The GI ("General Impression") column represents the overall curd quality on a scale of 1 (poor) to 5 (excellent). The "color" column presents the curd color at harvest on the Ctifl color chart with C3 indicating an intermediate color between C2 and C4.

The development of color and weight after harvest at controlled temperatures (5° C.) are assessed using 3 cycles with measurements taken every 7 days, having the latest cycle 21 days after harvest, one head per plot. The development of color and weight after harvest at ambient temperatures are taken using 2 cycles with measurements taken every 7 days, with the latest cycle 14 days after harvest, four heads per plot. The drymatter column provides the percentage of the curd from coldstorage.

TABLE 1

| Plot# | Diameter | Jacket | Self-covering | Weight | Depth | Fuzzynes | GI | Color |
|---|---|---|---|---|---|---|---|---|
| Replication 1 | | | | | | | | |
| 763 | 15.8 | 100 | 29 | 859 | 10.2 | 1 | 3 | 7 |
| 764 | 14.8 | 97 | 24 | 623 | 10.6 | 1 | 2 | 2 |
| 765 | 15.2 | 100 | 59 | 750 | 10.0 | 1 | 4 | 7 |

TABLE 1-continued

| | | | | | | | | |
|---|---|---|---|---|---|---|---|---|
| 768 | 14.0 | 78 | 7 | 435 | 8.1 | 2 | 1 | 5 |
| 769 | 15.2 | 100 | 48 | 781 | 9.5 | 1 | 4 | 2 |
| 771 | 14.6 | 100 | 52 | 763 | 11.0 | 1 | 4 | 3 |
| 773 | 16.8 | 100 | 83 | 1001 | 10.6 | 1 | 4 | 4 |
| 774 | 15.4 | 94 | 28 | 715 | 9.7 | 1 | 3 | 3 |
| 781 | 15.0 | 96 | 13 | 602 | 9.0 | 1 | 2 | 8 |
| 783 | 14.8 | 38 | 3 | 256 | 8.2 | 2 | 1 | 7 |
| Replication 2 | | | | | | | | |
| 784 | 15.2 | 100 | 36 | 700 | 9.5 | 1 | 4 | 3 |
| 785 | 13.0 | 78 | 5 | 275 | 7.0 | 2 | 2 | 4 |
| 787 | 15.5 | 100 | 62 | 699 | 10.3 | 1 | 4 | 8 |
| 788 | 14.7 | 97 | 44 | 679 | 9.2 | 1 | 3 | 3 |
| 792 | 15.0 | 100 | 36 | 646 | 9.7 | 1 | 4 | 8 |
| 793 | 16.1 | 100 | 67 | 1027 | 12.0 | 1 | 4 | 7 |
| 796 | 15.0 | 98 | 17 | 682 | 9.4 | 1 | 3 | 8 |
| 800 | 16.0 | 98 | 20 | 681 | 9.9 | 1 | 3 | 1 |
| 801 | 15.2 | 100 | 57 | 800 | 10.0 | 1 | 4 | 2 |
| 802 | 14.5 | 60 | 6 | 314 | 8.0 | 2 | 1 | 6 |
| Replication 3 | | | | | | | | |
| 805 | 14.2 | 28 | 7 | 237 | 6.7 | 2 | 1 | 7 |
| 807 | 16.0 | 100 | 86 | 937 | 10.6 | 1 | 4 | 6 |
| 808 | 15.2 | 100 | 23 | 675 | 9.8 | 1 | 3 | 2 |
| 809 | 14.8 | 98 | 20 | 824 | 10.1 | 1 | 3 | 2 |
| 810 | 15.6 | 100 | 21 | 814 | 9.8 | 1 | 4 | 9 |
| 811 | 16.4 | 100 | 36 | 1018 | 9.9 | 1 | 4 | 3 |
| 812 | 14.9 | 100 | 41 | 766 | 10.5 | 1 | 4 | 3 |
| 816 | 16.3 | 100 | 61 | 970 | 10.6 | 1 | 4 | 7 |
| 817 | 14.5 | 81 | 7 | 441 | 8.0 | 2 | 2 | 5 |
| 822 | 14.7 | 100 | 28 | 601 | 9.2 | 1 | 4 | 8 |

| | Weight and Color after harvest (coldstore 5° C.) | | | | | | Color after harvest (ambient conditions) | | Dry- |
|---|---|---|---|---|---|---|---|---|---|
| Plot# | hv wght | color | 1 (+7 DAYS) | | 2 (+14 DAYS) | | 3 (+21 DAYS) | 1 (+7 DAYS) | 2 (+14 DAYS) | matter |
| Replication 1 | | | | | | | | | | |
| 763 | 862 | 8 | 811 | 8 | 777 | 8 | 745 | 8 | 7 | 6 | 8.2 |
| 764 | 712 | 3 | 653 | 2 | 609 | 2 | 589 | 2 | 2 | 2 | 5.8 |
| 765 | 603 | 7 | 560 | 7 | 528 | 6 | 506 | 6 | 6 | 6 | 7.3 |
| 768 | 452 | 5 | 407 | 4 | 349 | 6 | 313 | 6 | 5 | 4 | 6.7 |
| 769 | 838 | 3 | 766 | 4 | 731 | 3 | 706 | 3 | 2 | 2 | 7.6 |
| 771 | 778 | 2 | 741 | 2 | 717 | 2 | 691 | 2 | 2 | 2 | 7.3 |
| 773 | 958 | 6 | 908 | 6 | 869 | 6 | 849 | 6 | 4 | 4 | 6.7 |
| 774 | 802 | 3 | 708 | 2 | 672 | 2 | 652 | 2 | 2 | 2 | 7.5 |
| 781 | 657 | 7 | 603 | 8 | 568 | 8 | 534 | 8 | 8 | 8 | 6.3 |
| 783 | 124 | 6 | 99 | 6 | 75 | 8 | 50 | 7 | 5 | X | 8.6 |
| Replication 2 | | | | | | | | | | |
| 784 | 691 | 4 | 626 | 4 | 589 | 3 | 559 | 3 | 2 | 2 | 6.2 |
| 785 | 275 | 4 | 231 | 4 | 200 | 7 | 172 | 7 | 5 | 5 | 9.1 |
| 787 | 626 | 7 | 586 | 8 | 582 | 7 | 536 | 7 | 7 | 6 | 6.1 |
| 788 | 656 | 3 | 603 | 2 | 570 | 2 | 540 | 2 | 3 | 2 | 6.9 |
| 792 | 560 | 8 | 511 | 8 | 483 | 8 | 467 | 7 | 7 | 6 | 7.1 |
| 793 | 1053 | 7 | 999 | 8 | 960 | 8 | 925 | 8 | 7 | 6 | 7.6 |
| 796 | 820 | 8 | 776 | 8 | 747 | 10 | 713 | 10 | 8 | 8 | 6.8 |
| 800 | 700 | 2 | 654 | 2 | 616 | 2 | 581 | 3 | 2 | 2 | 7.2 |
| 801 | 727 | 3 | 682 | 3 | 639 | 3 | 603 | 3 | 2 | 2 | 6.6 |
| 802 | 190 | 5 | 154 | 6 | 125 | 8 | 96 | 7 | 5 | 5 | 8.4 |
| Replication 3 | | | | | | | | | | |
| 805 | 210 | 6 | 157 | 6 | 124 | 8 | 99 | 8 | 6 | 6 | 8.4 |
| 807 | 898 | 7 | 850 | 7 | 802 | 6 | 778 | 5 | 6 | 5 | 6.1 |
| 808 | 761 | 2 | 707 | 1 | 666 | 2 | 624 | 2 | 3 | 2 | 6.9 |
| 809 | 883 | 3 | 831 | 4 | 798 | 4 | 778 | 4 | 3 | 2 | 9.9 |
| 810 | 887 | 9 | 843 | 8 | 808 | 9 | 771 | 9 | 8 | 10 | 6.4 |
| 811 | 1058 | 4 | 1027 | 4 | 975 | 4 | 946 | 4 | 3 | 2 | 5.5 |
| 812 | 827 | 3 | 793 | 2 | 758 | 1 | 740 | 2 | 4 | 3 | 7.0 |
| 816 | 1022 | 6 | 980 | 6 | 948 | 6 | 921 | 4 | 7 | 6 | 7.1 |
| 817 | 335 | 4 | 295 | 6 | 245 | 6 | 205 | 6 | 5 | 4 | 8.1 |
| 822 | 685 | 8 | 634 | 9 | 589 | 9 | 563 | 8 | 8 | 7 | 6.5 |

TABLE 1-continued

| Variety Replication Averages | Marker profile | | | | Diameter | Jacket | Selfcovering | Weight | Depth | Fuzzynes | GI | Color |
|---|---|---|---|---|---|---|---|---|---|---|---|---|
| | qtl1 | qtl2a | qtl2b | qtl7 | | | | | | | | |
| non BW controls | | | | | | | | | | | | |
| Fremont F1 | H | Y | Y | Y | 15.2 | 100 | 31 | 702 | 9.7 | 1 | 4 | 8 |
| Cornell F1 | Y | Y | W | Y | 16.1 | 100 | 77 | 879 | 10.5 | 1 | 4 | 6 |
| Aviron F1 | Y | Y | H | Y | 15.9 | 100 | 62 | 916 | 10.9 | 1 | 4 | 7 |
| Fortados OP | Y | Y | Y | Y | 15.2 | 98 | 17 | 699 | 9.4 | 1 | 3 | 8 |
| BW Sources | | | | | | | | | | | | |
| PI 183214 | W | W | — | — | 14.5 | 42 | 5 | 269 | 7.6 | 2 | 1 | 7 |
| NY6633 | W | W | W | W | 13.8 | 79 | 6 | 384 | 7.7 | 2 | 2 | 5 |
| BW elite lines | | | | | | | | | | | | |
| CLP/NY6633x9/FRE | W | W | W | W | 15.3 | 98 | 22 | 660 | 10.1 | 1 | 3 | 2 |
| CLPxNY6633 | W | W | W | W | 14.9 | 100 | 43 | 743 | 10.3 | 1 | 4 | 3 |
| 1BCSSxCLP/NY6633 | S | W | W | W | 15.6 | 100 | 47 | 866 | 9.8 | 1 | 4 | 2 |
| CLP/NY6633x9/FRE/CLP/NY6633/HOCe | W | W | W | W | 15.0 | 96 | 31 | 739 | 9.7 | 1 | 3 | 3 |

| Variety Replication Averages | Weight, % of original Weight and Color after harvest (coldstore 5° C.) | | | | | | | | | Date and Color after harvest (ambient conditions) | | Dry-matter |
|---|---|---|---|---|---|---|---|---|---|---|---|---|
| | hv wght | color | 1 | | 2 | | 3 | | | 1 | 2 | |
| non BW controls | | | | | | | | | | | | |
| Fremont F1 | 702 | 8 | 652 | 93 | 8 | 616 | 88 | 8 | 592 | 84 | 8 | 7 | 6 | 7.3 |
| Cornell F1 | 827 | 7 | 781 | 94 | 7 | 751 | 91 | 6 | 721 | 87 | 6 | 6 | 5 | 6.3 |
| Aviron F1 | 893 | 7 | 846 | 95 | 7 | 812 | 91 | 7 | 784 | 88 | 6 | 7 | 6 | 7.3 |
| Fortados OP | 788 | 8 | 741 | 94 | 8 | 708 | 90 | 9 | 673 | 85 | 9 | 8 | 9 | 6.5 |
| BW Sources | | | | | | | | | | | | |
| PI 183214 | 175 | 6 | 137 | 78 | 6 | 108 | 62 | 8 | 82 | 47 | 7 | 5 | 6 | 8.5 |
| NY6633 | 354 | 4 | 311 | 88 | 5 | 265 | 75 | 6 | 230 | 65 | 6 | 5 | 4 | 8.0 |
| BW elite lines | | | | | | | | | | | | |
| CLP/NY6633x9/FRE | 724 | 2 | 671 | 93 | 2 | 630 | 87 | 2 | 598 | 83 | 2 | 2 | 2 | 6.6 |
| CLPxNY6633 | 765 | 3 | 720 | 94 | 3 | 688 | 90 | 2 | 663 | 87 | 2 | 3 | 2 | 6.8 |
| 1BCSSxCLP/NY6633 | 874 | 3 | 825 | 94 | 4 | 782 | 89 | 3 | 752 | 86 | 3 | 2 | 2 | 6.6 |
| CLP/NY6633x9/FRE/CLP/NY6633/HOCe | 780 | 3 | 714 | 92 | 3 | 680 | 87 | 3 | 657 | 84 | 3 | 3 | 2 | 8.1 |

| Average of classes | Marker profile | | | | Diameter | Jacket | Self-covering | Weight | Depth | Fuzzyness | GI | Color |
|---|---|---|---|---|---|---|---|---|---|---|---|---|
| | qtl1 | qtl2a | qtl2b | qtl7 | | | | | | | | |
| non BW controls: | | | | | | | | | | | | |
| Fremont F1 | H | Y | Y | Y | 15.2 | 100 | 31 | 702 | 97 | 1 | 4 | 8 |
| Cornell F1 | Y | Y | W | Y | 16.1 | 100 | 77 | 879 | 105 | 1 | 4 | 6 |
| Aviron F1 | Y | Y | H | Y | 15.9 | 100 | 62 | 916 | 109 | 1 | 4 | 7 |
| Fortados OP | Y | Y | Y | Y | 15.2 | 98 | 17 | 699 | 94 | 1 | 3 | 8 |
| average: | | | | | 15.6 | 100 | 47 | 799 | 101 | 1 | 4 | 7 |
| BW sources: | | | | | | | | | | | | |
| PI 183214 | W | W | ? | ? | 14.5 | 42 | 5 | 269 | 76 | 2 | 1 | 7 |
| NY6633 | W | W | W | W | 13.8 | 79 | 6 | 384 | 77 | 2 | 2 | 5 |
| average: | | | | | 14.2 | 61 | 6 | 327 | 77 | 2 | 2 | 6 |
| BW elite lines: | | | | | | | | | | | | |
| CLP/NY6633x9/FRE | W | W | W | W | 15.3 | 98 | 22 | 660 | 101 | 1 | 3 | 2 |
| CLPxNY6633 | W | W | W | W | 14.9 | 100 | 43 | 743 | 103 | 1 | 4 | 3 |

TABLE 1-continued

| | | | | | | | | | | | | | |
|---|---|---|---|---|---|---|---|---|---|---|---|---|---|
| 1BCSSxCLP/NY6633 | S | W | W | W | 15.6 | 100 | 47 | 866 | 98 | | 1 | 4 | 2 |
| CLP/NY6633x9/FRE/CLP/NY6633/HOCe | W | W | W | W | 15.0 | 96 | 31 | 739 | 97 | | 1 | 3 | 3 |
| average: | | | | | 15.2 | 99 | 36 | 752 | 100 | | 1 | 4 | 3 |

| Average of classes | Weight, % of original Weight and Color after harvest (coldstore 5° C.) | | | | | | | | | Date and Color after harvest (ambient conditions) | | Dry-matter |
|---|---|---|---|---|---|---|---|---|---|---|---|---|
| | hv wght | color | 1 | | 2 | | 3 | | | 1 | 2 | |
| non BW controls: | | | | | | | | | | | | |
| Fremont F1 | 702 | 8 | 652 | 93 | 8 | 616 | 88 | 8 | 592 | 84 | 8 | 7 | 6 | 7.3 |
| Cornell F1 | 827 | 7 | 781 | 94 | 7 | 751 | 91 | 6 | 721 | 87 | 6 | 6 | 5 | 6.3 |
| Aviron F1 | 893 | 7 | 846 | 95 | 7 | 812 | 91 | 7 | 784 | 88 | 6 | 7 | 6 | 7.3 |
| Fortados OP | 788 | 8 | 741 | 94 | 8 | 708 | 90 | 9 | 673 | 85 | 9 | 8 | 9 | 6.5 |
| average: | | 8 | | 94 | 8 | | 90 | 8 | | 86 | 8 | 7 | 7 | 6.9 |
| BW sources: | | | | | | | | | | | | | | |
| PI 183214 | 175 | 6 | 137 | 78 | 6 | 108 | 62 | 8 | 82 | 47 | 7 | 5 | 6 | 8.5 |
| NY6633 | 354 | 4 | 311 | 88 | 5 | 265 | 75 | 6 | 230 | 65 | 6 | 5 | 4 | 8.0 |
| average: | | 5 | | 83 | 6 | | 69 | 7 | | 56 | 7 | 5 | 5 | 8.3 |
| BW elite lines: | | | | | | | | | | | | | | |
| CLP/NY6633x9/FRE | 724 | 2 | 671 | 93 | 2 | 630 | 87 | 2 | 598 | 83 | 2 | 2 | 2 | 6.6 |
| CLPxNY6633 | 765 | 3 | 720 | 94 | 3 | 688 | 90 | 2 | 663 | 87 | 2 | 3 | 2 | 6.8 |
| 1BCSSxCLP/NY6633 | 874 | 3 | 825 | 94 | 4 | 782 | 89 | 3 | 752 | 86 | 3 | 2 | 2 | 6.6 |
| CLP/NY6633x9/FRE/CLP/NY6633/HOCe | 780 | 3 | 714 | 92 | 3 | 680 | 87 | 3 | 657 | 84 | 3 | 3 | 2 | 8.1 |
| average: | | 3 | | 93 | 3 | | 88 | 3 | | 85 | 3 | 3 | 2 | 7.0 |

Example 6. Cauliflower Growth Chamber Trials

Cauliflower seeds are initially planted in a greenhouse. After about 10 weeks of growth, seedlings are transplanted to container pots (10 L). After an additional three weeks of growth, container pots are placed in a growth chamber (GTI Zephyr Koudetechniek B V, Groningen, Netherlands). Plants are grown in RSEO2 potting soil. Plants are grown at 15° C. with light conditions of about 7500 LUX, Philips Son T plus 400 W lage druk natrium, Phillips bulb 'Peer' 40W, HPI-T 400W metaalhalogeen). The self-covering inner leaves are not removed. Curd color is evaluated as described below in Example 7 from curds of 2 plants per line.

Curds from growth chamber trials are stored under growth chamber conditions. Development of color and weight after harvest at growth chamber conditions (15° C.) is analyzed in 5 cycles with measurements about every 3 days, with the latest cycle measured at 15 days after harvest.

Growth chamber data is shown in Table 2, below.

TABLE 2

| Line | Diameter | Weight | Depth | Fuzzyness | GI | Color |
|---|---|---|---|---|---|---|
| replication1: | | | | | | |
| NON BW CONTROLS: | | | | | | |
| Fremont F1 | 11.0 | 235 | 7.9 | 1 | 5 | 7 |
| Cornell F1 | 11.5 | 293 | 8.2 | 1 | 5 | 5 |
| Aviso F1 | 10.5 | 260 | 7.5 | 1 | 4 | 6 |
| Fortados OP | 11.0 | 186 | 7.3 | 1 | 4 | 8 |
| BW SOURCES: | | | | | | |
| PI 183214 | 11.5 | 84 | 5.5 | 2 | 1 | 4 |
| NY6633 | 11.0 | 111 | 5.6 | 2 | 2 | 5 |
| BW ELITE LINES: | | | | | | |
| CLP/NY6633 × 9/Fre | 11.0 | 196 | 7.6 | 1 | 3 | 1 |
| CLP × NY6633 | 11.0 | 232 | 8.0 | 1 | 4 | 1 |

TABLE 2-continued

| | | | | | | | |
|---|---|---|---|---|---|---|---|
| 1BCSS × CLP/NY6633 | 11.5 | | 258 | 8.0 | 1 | 4 | 1 |
| CLP/NY6633x9/Fre/CLP/NY6633/HOCe | 11.0 | | 201 | 7.4 | 1 | 4 | 1 |
| replication2: NON BW CONTROLS: | | | | | | | |
| Fremont F1 | 11.0 | | 249 | 7.9 | 1 | 5 | 7 |
| Cornell F1 | 11.0 | | 268 | 7.8 | 1 | 5 | 4 |
| Aviso F1 | 11.5 | | 282 | 8.0 | 1 | 5 | 6 |
| Fortados OP | 10.5 | | 189 | 7.2 | 1 | 4 | 8 |
| BW SOURCES: | | | | | | | |
| PI 183214 | 10.5 | | 54 | 5.2 | 1 | 1 | 4 |
| NY6633 | 11.5 | | 141 | 6.5 | 2 | 2 | 3 |
| BW ELITE LINES: | | | | | | | |
| CLP/NY6633 × 9/Fre | 11.0 | | 206 | 7.9 | 1 | 3 | 2 |
| CLP × NY6633 | 11.0 | | 251 | 7.9 | 1 | 5 | 2 |
| 1BCSS × CLP/NY6633 | 10.5 | | 208 | 7.6 | 1 | 5 | 1 |
| CLP/NY6633x9/Fre/CLP/NY6633/HOCe | 11.0 | | 188 | 7.1 | 1 | 4 | 1 |

| | Day of month, Color and Weight after harvest (ambient conditions) | | | | | | | | | | | | |
|---|---|---|---|---|---|---|---|---|---|---|---|---|---|
| Line | 1 | | | 2 | | | 3 | | | 4 | | 5 | Drymatter |
| replication 1: NON BW CONTROLS: | | | | | | | | | | | | | |
| Fremont F1 | 14 | 8 | 226 | 17 | 7 | 213 | 20 | 8 | 191 | 23 | 8 | 176 26 | 7 157 6.7 |
| Cornell F1 | 20 | 5 | 274 | 23 | 5 | 257 | 26 | 5 | 239 | 30 | 4 | 209 02 | 4 186 5.9 |
| Aviso F1 | 02 | 7 | 243 | 06 | 7 | 220 | 09 | 7 | 166 | 13 | 7 | 126 16 | 7 109 9.2 |
| Fortados OP | 02 | 8 | 173 | 06 | 8 | 159 | 09 | 8 | 151 | 12 | 8 | 138 14 | 8 131 6.0 |
| BW SOURCES: | | | | | | | | | | | | | |
| PI 183214 | 09 | 3 | 64 | 12 | 3 | 42 | 14 | 4 | 33 | 17 | BRWN | 20 20 | BRWN 14 8.5 |
| NY6633 | 03 | 5 | 95 | 06 | 4 | 81 | 09 | 4 | 72 | 12 | 4 | 59 14 | 3 51 6.1 |
| BW ELITE LINES: | | | | | | | | | | | | | |
| CLP/NY6633 × 9/Fre | 14 | 1 | 188 | 17 | 1 | 179 | 20 | 1 | 160 | 23 | 1 | 143 26 | 1 125 6.7 |
| CLP × NY6633 | 17 | 2 | 213 | 20 | 2 | 184 | 23 | 2 | 163 | 26 | 2 | 136 30 | 3 105 8.1 |
| 1BCSS × CLP/NY6633 | 12 | 1 | 234 | 14 | 1 | 221 | 17 | 1 | 196 | 20 | 1 | 172 23 | 1 149 6.2 |
| CLP/NY6633x9/Fre/CLP/NY6633/HOCe | 12 | 1 | 191 | 17 | 1 | 179 | 20 | 1 | 158 | 23 | 1 | 146 26 | 1 128 7.2 |
| replication2: NON BW CONTROLS: | | | | | | | | | | | | | |
| Fremont F1 | 14 | 7 | 236 | 17 | 7 | 219 | 20 | 7 | 200 | 23 | 7 | 184 26 | 6 163 6.4 |
| Cornell F1 | 23 | 4 | 242 | 26 | 4 | 221 | 30 | 4 | 191 | 02 | 4 | 171 06 | 4 146 6.6 |
| Aviso F1 | 20 | 6 | 258 | 23 | 6 | 243 | 26 | 6 | 219 | 30 | 5 | 188 02 | 5 169 5.5 |
| Fortados OP | 06 | 8 | 170 | 09 | 7 | 160 | 12 | 7 | 147 | 14 | 6 | 140 17 | 7 125 5.7 |
| BW SOURCES: | | | | | | | | | | | | | |
| PI 183214 | 06 | 4 | 30 | 09 | 4 | 20 | 12 | BRWN | 12 | 14 | BRWN | 9 17 | BRWN 7 8.1 |
| NY6633 | 02 | 4 | 123 | 06 | 4 | 102 | 09 | 3 | 89 | 12 | 3 | 72 14 | 2 64 6.1 |
| BW ELITE LINES: | | | | | | | | | | | | | |
| CLP/NY6633 × 9/Fre | 20 | 2 | 182 | 23 | 2 | 167 | 26 | 2 | 149 | 30 | 2 | 120 02 | 2 108 7.2 |
| CLP × NY6633 | 12 | 2 | 237 | 14 | 2 | 226 | 17 | 1 | 204 | 20 | 1 | 180 23 | 1 161 6.7 |
| 1BCSS × CLP/NY6633 | 03 | 1 | 192 | 06 | 2 | 178 | 09 | 1 | 165 | 12 | 1 | 151 14 | 1 144 5.2 |
| CLP/NY6633x9/Fre/CLP/NY6633/HOCe | 09 | 1 | 173 | 12 | 1 | 156 | 14 | 1 | 146 | 17 | 1 | 127 20 | 1 110 6.2 |

| Line Averages of replications | Diameter | Weight | Depth | Fuzzyness | GI | Color |
|---|---|---|---|---|---|---|
| NON BW CONTROLS | | | | | | |
| Fremont F1 | 11.0 | 242 | 79 | 1 | 5 | 7 |
| Cornell F1 | 11.3 | 281 | 80 | 1 | 5 | 5 |
| Aviso F1 | 11.0 | 271 | 78 | 1 | 5 | 6 |
| Fortados OP | 10.8 | 188 | 73 | 1 | 4 | 8 |
| average | 11.0 | 246 | 78 | 1 | 5 | 7 |
| BW SOURCES | | | | | | |
| PI 183214 | 11.0 | 69 | 54 | 2 | 1 | 4 |
| NY6633 | 11.3 | 126 | 61 | 2 | 2 | 4 |
| average | 11.2 | 98 | 58 | 2 | 2 | 4 |

TABLE 2-continued

| BW ELITE LINES | | | | | | |
|---|---|---|---|---|---|---|
| CLP/NY6633 × 9/Fre | 11.0 | 201 | 78 | 1 | 3 | 2 |
| CLP × NY6633 | 11.0 | 242 | 80 | 1 | 5 | 2 |
| 1BCSS × CLP/NY6633 | 11.0 | 233 | 78 | 1 | 5 | 1 |
| CLP/NY6633x9/Fre/CLP/NY6633/HOCe | 11.0 | 195 | 73 | 1 | 4 | 1 |
| average | 11.0 | 218 | 77 | 1 | 4 | 2 |

| Line Averages of replications | Color and Weight after harvest (ambient conditions) | | | | | | | | | Drymatter |
|---|---|---|---|---|---|---|---|---|---|---|
| | 1 | | 2 | | 3 | 4 | | 5 | % of original weight (corrected to 15 days) | |
| NON BW CONTROLS | | | | | | | | | | |
| Fremont F1 | 8 | 231 | 7 | 216 | 8 | 196 | 8 | 180 | 7 | 160 | 64 | 6.6 |
| Cornell F1 | 5 | 258 | 5 | 239 | 5 | 215 | 4 | 190 | 4 | 166 | 67 | 6.4 |
| Aviso F1 | 7 | 251 | 7 | 232 | 7 | 193 | 6 | 157 | 6 | 139 | 56 | 7.4 |
| Fortados OP | 8 | 172 | 8 | 160 | 8 | 149 | 7 | 139 | 8 | 128 | 68 | 5.9 |
| average | 7 | | 7 | | 7 | 6 | 6 | 64 | | | | 6.6 |
| BW SOURCES | | | | | | | | | | |
| PI 183214 | 4 | 47 | 4 | 31 | 4 | 23 | x | 15 | x | 11 | 14 | 8.3 |
| NY6633 | 5 | 109 | 4 | 92 | 4 | 81 | 4 | 66 | 3 | 58 | 47 | 6.1 |
| average | 5 | | 4 | | 4 | (4) | | (3) | | | 31 | 7.2 |
| BW ELITE LINES | | | | | | | | | | |
| CLP/NY6633 × 9/Fre | 2 | 185 | 2 | 173 | 2 | 155 | 2 | 132 | 2 | 117 | 58 | 7.0 |
| CLP × NY6633 | 2 | 225 | 2 | 205 | 2 | 183 | 2 | 158 | 2 | 133 | 52 | 7.4 |
| 1BCSS × CLP/NY6633 | 1 | 221 | 2 | 200 | 1 | 181 | 1 | 162 | 1 | 147 | 62 | 5.7 |
| CLP/NY6633x9/Fre/CLP/NY6633/HOCe | 1 | 182 | 1 | 168 | 1 | 152 | 1 | 137 | 1 | 117 | 57 | 6.7 |
| average | 2 | | 2 | | 2 | 2 | | 2 | | | 57 | 6.7 |

Example 7. Evaluation of Cauliflower Curd Color

Cauliflower curds are compared to Ctifl color standards (Centre technique interprofessionnel des fruits et legumes, France) and an integer value is assigned. The Ctifl color code comprises five categories that increase from more white to more yellow color: C2 ("blanc"), C4 ("crème"), C6 ("ivoire"), C8 ("jaune pale") and C10 ("jaune"). In the case of curd color that is whiter than C2, the RAL standard chip 9010 is used. For example, a color score of zero (0) is assigned to a curd having color closest to RAL standardchip 9010; a color score of one (1) is assigned to a curd having color between RAL standardchip 9010 and Ctifl color C2; a color score of two (C2) is assigned to a curd having color closest to Ctifl color C2; a color score of three (C3) is assigned to a curd having color between Ctifl color C2 and Ctifl color C4; and a color score of four (C4) is assigned to a curd having color closest to Ctifl color C4. A curd having a color between two colors is assigned a color score intermediate of the two colors. The color score assigned to a cauliflower line is derived by determining the average color score of 15 curds at harvest, 3 went into cold room and 12 at ambient sample curds from that line.

Example 8. Mapping Quantitative Trait Loci for the Brilliant White Phenotype in Cauliflower Cauliflower lines ED37 and NY6633 are crossed and one of the $F_1$ plants is used to create 500 Doubled Haploid (DH) plants. Line ED37 is a non-brilliant white, non-persistent white line and line NY6633 is a persistent white line.

The DH plants are propagated and clones are created for two field trials. In each field trial, curd whiteness is measured 3 times after exposure to light. Variation among the 6 replications is calculated, and the 94 DH plants with the lowest standard deviations are used to develop a molecular map.

The mapping software Joinmap®, version 3.0 (Kyazma B. V., Wageningen, The Netherlands) is used to create a molecular map with the 94 DH plants. Mapping is performed using pair wise recombination estimations and calculated using the Haldane mapping function of the software. With a LOD setting of 5, nine linkage groups, which match the number of chromosomes in Brassica oleraceae, are identified.

The average measurements for brilliant white and the marker data from the 94 DH lines are used for QTL mapping with the MapQTL® software, version 4 (Kyazma B. V., Wageningen, The Netherlands). Using a LOD score of 2.5 as a cut off for significance, five QTLs are identified. One QTL is found on linkage groups O1, O7, and O9 and two QTLs are found on linkage group O2. FIG. 1. The QTLs are identified as QTLO1, QTLO2a, QTLO2b, QTLO7, and QTLO9. An epistatic interaction is identified between the QTLs on linkage groups O1 and O9.

Position and effects of QTLs exceeding the threshold value are also determined (Table 2). Position is determined by chromosome, position on the chromosome (in cM) and the one-LOD-drop interval is also determined. Kruskall wallis analyses by interval mapping and R-square values, is used to determine the effects of the QTLs.

TABLE 3

| QTL | Marker | Chromosome | position | One LOD drop interval (in cM) | Kruskall wallis analyses |
|---|---|---|---|---|---|
| O1 | sN2176Fa | O1 | 4.7 | 4.1-5.3 | 43.5 ($p \le 0.1 \cdot 10^{-3}$) |
| with only NY66 allele at O9 | sN2176Fa | O1 | | | 49.8 ($p \le 0.1 \cdot 10^{-3}$) |
| with only ED37 allele at O9 | sN2176Fa | O1 | | | 2.6 (ns) |
| O2a | PATGMTAT446ED37scar | O2 | 6.6 | 0-43.6 | 16.3 ($p < 0.5 \cdot 10^{-3}$) |
| O2b | BH464729 | O2 | 33.6 | 0-43.6 | 13.3 ($p < 0.5 \cdot 10^{-3}$) |
| O7 | BH458678 | O7 | 94.9 | 61.5-94.9 | 11.2 ($p < 0.1 \cdot 10^{-2}$) |
| O9 | BH576393 | O9 | 17.8 | 0-22.6 | 11.7 ($p < 0.1 \cdot 10^{-2}$) |
| with only NY66 allele at O1 | BH576393 | O9 | | | 20.8 ($p < 0.1 \cdot 10^{-3}$) |
| with only ED37 allele at O1 | BH576393 | O9 | | | 0.8 (ns) |

| | interval mapping | | | |
|---|---|---|---|---|
| QTL | Peak LOD score | % var explained | Allelic effect (in trait value) | R square |
| O1 | 13.22 | 27.5 | 0.95 | 0.254 |
| with only NY66 allele at O9 | 14.94 | 41.8 | 1.23 | |
| with only ED37 allele at O9 | 0.04 | 0.3 | 0.07 | |
| O2a | 3.16 | 7.4 | 0.47 | 0.074 |
| O2b | 2.78 | 6.7 | 0.48 | 0.068 |
| O7 | 2.87 | 6.7 | 0.48 | 0.061 |
| O9 | 2.91 | 6.9 | 0.47 | 0.072 |
| with only NY66 allele at O1 | 5.21 | 30.5 | 1.14 | |
| with only ED37 allele at O1 | 0.04 | 0.1 | 0.05 | |

Interval mapping plots for the white curd trait in cauliflower of chromosomes O1, O2, O7, and O9 are provided in FIGS. 1, 2, and 3. Plots of the these four chromosomes show significant LOD values (Y-ax) exceeding LOD 2.5. FIG. 1. This genome wide threshold, calculated by applying a permutation test, is indicated with a dashed-line in FIG. 1. The x-axes in the plots are the respective linkage groups, marker loci are reflected with small arrows and distances are given (in cM). The large bold arrows with the names O1, O2a, O2b, O7, and O9 are the most closely linked marker loci within a particular QTL. FIG. 2 provides an interval mapping plot for the white curd trait in cauliflower of chromosome O1. The upper plot is constructed with the lines having the ED37 allele at marker locus O9. The lower plot is constructed with the lines having the NY66 allele at marker locus O9. The genome wide LOD (Y-ax) threshold, calculated by applying permutation tests is 3.5 for the plot with ED37 allele at O9 and is 3.7 for the plot with NY66 allele at O9. FIG. 3 provides an interval mapping plot for the white curd trait in cauliflower of chromosome O9. The upper plot is constructed with the lines having the ED37 allele at the marker locus O1. The lower plot is constructed with the lines having the NY66 allele at marker locus O1. The genome wide LOD (Y-ax) threshold, calculated by applying permutation tests is 4.5 for the plot with ED37 allele at O9 and is 3.2 for the plot with NY66 allele at O9.

TaqMan® analysis of QTLO1 and QTLO2a is performed as follows. PCR reactions contain 1.4 microliters of DNA, 5.0 microliters Platinum qPCR-Supermix (Invitrogen, Paisley UK; catalog number 11730-O25), 0.2 microliters 50×ROX Reference dye (Invitrogen, Paisely, UK), 0.2 microliters PCR primers (from a stock solution containing 36 μM of each primer), 0.2 microliters TaqMan® probe primers (from a stock solution containing 8 μM of each primer), and 3.0 microliters of sterile water. PCR reactions are incubated for 2 minutes at 50° C., 2 minutes at 94° C., followed by 40 cycles of 15 seconds at 94° C., and 1 minute at 60° C. PCR reactions are performed on an ABI9700 PCR machine (Applied Biosystems, Foster City, CA). After completion of the PCR reaction, allele detection is performed with an ABI7000 instrument (Applied Biosystems, Foster City, CA), following the instructions provided by the manufacture.

Exemplary primer sequences used in the TaqMan® analysis of QTLO1 are as follows. SEQ ID NO: 2 is a PCR primer for the O1 QTL TaqMan® assay: 5' AGCTTCAGCAAAGTCACTCTCTT (SEQ ID NO: 2). SEQ ID 3 is a PCR primer for the O1 QTL TaqMan® assay: 5' AGAGTGAGAAGACGCTTGAGTTC (SEQ ID NO: 3). SEQ ID 4 is a TaqMan® probe primer for the O1 QTL assay: 5' VIC CGAGCTGGCCGAGAA (SEQ ID NO: 4). SEQ ID 5 is a TaqMan® probe primer for the O1 QTL assay: 5' FAM ACGAGCTGACCGAGAA (SEQ ID NO: 5).

Sequence of a marker near the "white" allele at QTLO1 is shown in SEQ ID NO: 1. A single nucleotide polymorphism between the donor NY6633 and recipient ED37 parents is identified within SEQ ID NO: 1 at position 56 (a C or T).

Exemplary primer sequences used in the TaqMan® analysis of QTLO2a are as follows. SEQ ID NO: 7 is a PCR primer for the O2a QTL TaqMan® assay: 5' TCAGTTTT-CAAACAGTAACCATTTTGTTCAT (SEQ ID NO: 7). SEQ ID NO: 8 is a PCR primer for the O2a QTL TaqMan® assay: 5' ATGATGGCTGGTGCTTGGA (SEQ ID NO: 8). SEQ ID NO: 9 is a TaqMan® probe primer for the O2a QTL assay: 5' FAM-AACAGCGACATGAAT (SEQ ID NO: 9). SEQ ID NO: 10 is a TaqMan® probe primer for the O2a QTL assay.: 5' VIC-AAGAACAGCGATATGAAT (SEQ ID NO: 10).

Sequence of a marker near the "white" allele at QTLO2a is shown in SEQ ID NO: 6. A single nucleotide polymorphism between the donor NY6633 and recipient ED37 parents is located at position 187 (C to T).

CAPS analysis of QTLO2b is performed as follows. PCR reactions contain 2.0 microliters 10×PCR buffer (Invitrogen, Paisley, UK), 0.8 microliters 50 mM MgCl$_2$, 0.8 microliters of a stock solution containing 2.5 mM of each dNTP, 0.4 microliters 10 μM SEQ ID NO: 12 primer, 0.4 microliters 10 μM SEQ ID NO: 13 primer, 0.1 microliters Taq polymerase (Invitrogen, Paisley, UK, catalog #10342-020), 1.0 microliters DNA (about 10-100 ng) and 14.5 microliters sterile water. PCR reactions are incubated for 2 minutes at 94° C. followed by 35 cycles of 60 seconds at 92° C., then 30 seconds at 52° C., then 1 minute at 72° C. PCR reactions are then incubated for 5 minutes at 72° C. Post-PCR incubation with Tsp509I restriction enzyme is performed in a reaction containing 20.0 microliters PCR reaction, 3.0 microliters NEB buffer #1 (New England Biolabs, Leusden, The Netherlands; catalog number B7001S), 6.8 microliters sterile water, and 0.2 microliters Tsp509I restriction enzyme (New England Biolabs, Leusden, The Netherlands; catalog number R0149L). This reaction is incubated for 3-4 hours at 65C°. Following the restriction enzyme digest, reaction products are electrophoretically resolved on a 1.2% w/v agarose gel (Biometra, Leusden, The Netherlands; catalog number 21069158). Molecular mass standards from Invitrogen, (Paisley, UK) are included in an adjacent gel lane to estimate the fragment sizes. Samples that are homozygous for the 'yellow' O2b allele produce fragments of about 400 and about 180 base pairs, and samples that are homozygous for the 'white' O2b allele produce fragments of about 580 base pairs. Samples that are heterozygous at this locus produce all three fragments.

Exemplary primer sequences used in the CAPS analysis of QTLO2b are as follows. SEQ ID NO: 12 is a PCR primer for the O2b CAPS assay: 5'CCATAGTCCATAACTGTTT-CATGC (SEQ ID NO: 12). SEQ ID NO: 13 is a PCR primer for the O2b CAPS assay: 5' CACAGGCAAAC-CAAACACAC (SEQ ID NO: 13).

Sequence of a marker near the "white" allele at QTLO2b is shown in SEQ ID NO: 11. A single nucleotide polymorphism between the donor NY6633 and recipient ED37 parents is located at position 418 (A to T). Restriction sites for Tsp509I are also located within SEQ ID NO: 11.

INDEL analysis of QTLO7a is performed as follows. PCR reactions contained 2.0 microliters 10×PCR buffer (Invitrogen, Paisley, UK), 0.8 microliters 50 mM MgCl$_2$, 0.8 microliters of a stock solution containing 2.5 mM of each dNTP, 0.4 microliters 10 μM SEQ ID 15 primer, 0.4 microliters 10 μM SEQ ID 16 primer, 0.1 microliters Taq polymerase (Invitrogen, Paisley, UK; catalog number 10342-020), 1.0 microliters DNA (about 10-100 ng), and 14.5 microliters sterile water. PCR reactions are incubated for 2 minutes at 94° C., followed by 35 cycles of 60 seconds at 92° C., then 30 seconds at 52° C., then 1 minute at 72° C. PCR reactions are then incubated for 5 minutes at 72° C.

Following PCR, the reaction products are electrophoretically resolved on a 1.2% w/v agarose gel (Biometra, Leusden, The Netherlands; catalog number 21069158). Molecular mass standards from Invitrogen, (Paisley, UK), are included in an adjacent gel lane to estimate the fragment sizes. Samples that are homozygous for the 'yellow' O7 allele produce a fragment of about 700 base pairs, and samples that are homozygous for the 'white' O7 allele produce a fragment of about 930 base pairs. Samples that are heterozygous at this locus produce both fragments.

Exemplary primer sequences used in the INDEL analysis of QTLO7 are as follows. SEQ ID NO: 15 is a PCR primer for the O7 INDEL assay: 5' TTTTGTTTTGTTTTATG-CATGTTTC (SEQ ID NO: 15). SEQ ID NO: 16 is a PCR primer for the O7 INDEL assay: 5' GTAATGCTTCAAGA-TATGGAGAATG (SEQ ID NO: 16).

Sequence of a marker near the "white" allele at QTLO7 is shown in SEQ ID NO: 14. An INDEL polymorphism between the donor NY6633 and recipient ED37 parents is highlighted in FIG. 4. The INDEL polymorphism is underlined and the ED37 recipient sequence is provided in the lower lines.

CAPS analysis of QTLO9 is performed as follows. PCR reactions contained 2.0 microliters 10×PCR buffer (Invitrogen, Paisley, UK), 0.8 microliters 50 mM MgCl$_2$, 0.8 microliters of a stock solution containing 2.5 mM of each dNTP. 0.4 microliters 10 μM SEQ ID NO: 18 primer, 0.4 microliters 10 μM SEQ ID NO: 19 primer, 0.1 microliters Taq polymerase (Invitrogen, Paisley, UK, catalog #10342-O20), 1.0 microliters DNA and 14.5 microliters sterile water. PCR reactions are incubated for 2 minutes at 94° C., followed by 35 cycles of 60 seconds at 92° C., then 30 seconds at 52° C., then 1 minute at 72° C. PCR reactions are then incubated for 5 minutes at 72° C. Post-PCR incubation with BstUI restriction enzyme is performed in a reaction containing 20.0 microliters PCR reaction, 3.0 microliters NEB buffer #2 (New England Biolabs, Leusden, The Netherlands; catalog number B7002S), 6.8 microliters sterile water, and 0.2 microliters BstUI restriction enzyme (New England Biolabs, Leusden, The Netherlands; catalog number #R0518L, 10 units/ul). This reaction is incubated for 3-4 hours at 60C°. Following the restriction enzyme digest, reaction products are electrophoretically resolved on a 1.2% w/v agarose gel (Biometra, Leusden, The Netherlands; catalog number 21069158). Molecular mass standards from Invitrogen, (Paisley, UK) are included in an adjacent gel lane to estimate the fragment sizes. Samples that are homozygous for the 'yellow' O9 allele produce fragments of about 305, about 223, about 109, and about 76 base pairs, and samples that are homozygous for the 'white' O9 allele produced fragments of about 382, about 223, and about 109 base pairs. Samples that are heterozygous at this locus produce all five fragments.

Exemplary primer sequences used in the CAPS analysis of QTLO9 are as follows. SEQ ID NO: 18 is a PCR primer for the O9 CAPS assay: 5' AGAAGGGTACATCCC-CAAGG (SEQ ID NO: 18). SEQ ID NO: 19 is a PCR primer for the O9 CAPS assay: 5' CTTTGTGCGACGGTGAGAG (SEQ ID NO: 19).

Sequence of a marker near the "white" allele at QTLO9 is shown in SEQ ID NO: 17. A single nucleotide polymorphism between the donor NY6633 and recipient ED37 parents is located at position 268 (A to G). The restriction sites for BstUI are located within SEQ ID NO: 17, with an additional site located within the recipient sequence.

Plant material from cauliflower lines from different selection years is analyzed for markers linked to the five QTLs associated with the brilliant white phenotype in either field-grown plants or greenhouse-grown plants. In addition, the cauliflower heads are scored for color as described in Example 3 above.

Example 9. Identification of Additional Sources of QTLs

Fifty-four commercially available cauliflower varieties (hybrids) are screened for markers associated with the five QTLs associated with the white curd phenotype. The results of the analysis are provided in Table 4.

TABLE 4

| Variety (Company) | Segment | QTLO1 | QTLO2A | QTLO2B | QTLO7 | QTLO9 |
|---|---|---|---|---|---|---|
| BALBOA (Bejo) | Summer cauliflower | Yellow | Yellow | Yellow | H | H |
| BELOT (Bejo) | late autumn cauliflower | Yellow | Yellow | Yellow | Yellow | Yellow |
| JEREZ (Bejo) | Summer cauliflower | Yellow | Yellow | Yellow | H | H |
| SEVILLA (Bejo) | Summer cauliflower | H | Yellow | Yellow | Yellow | H |
| SKYWALKER (Bejo) (Company) | Summer cauliflower | Yellow | Yellow | Yellow | Yellow | H |
| AVIRON (Clause) | Summer cauliflower | Yellow | Yellow | Yellow | Yellow | H |
| BELUGA (Clause) | Summer cauliflower | Yellow | Yellow | Yellow | Yellow | H |
| DELFINO (Clause) | Summer cauliflower | H | Yellow | Yellow | Yellow | Yellow |
| MERIDIEN (Clause) | Summer cauliflower | H | Yellow | H | Yellow | White |
| MOBY DICK (Clause) | Summer cauliflower | Yellow | Yellow | Yellow | Yellow | H |
| NESSIE (Clause) | Summer cauliflower | H | Yellow | Yellow | Yellow | Yellow |
| RAFALE (Clause) | late autumn cauliflower | White | Yellow | H | Yellow | White |
| REDOUTABLE (Clause) | winter cauliflower | Yellow | Yellow | Yellow | White | White |
| ELINIA (Enza) | Summer cauliflower | Yellow | Yellow | Yellow | Yellow | Yellow |
| VALTOS (Enza) | Summer cauliflower | H | Yellow | Yellow | Yellow | H |
| VERONIE (Enza) | Summer cauliflower | Yellow | Yellow | Yellow | H | Yellow |
| VIVIANE (Enza) | Summer cauliflower | Yellow | Yellow | Yellow | Yellow | Yellow |
| XENIA (Enza) | Summer cauliflower | H | Yellow | Yellow | Yellow | Yellow |
| DENIOL (OBS) | winter cauliflower | H | White | Yellow | Yellow | White |
| JEF (OBS) | winter cauliflower | H | H | Yellow | H | White |
| JULUAN (OBS) | winter cauliflower | H | White | Yellow | Yellow | White |
| MILIAU (OBS) | winter cauliflower | H | White | H | H | White |
| NELIG (OBS) | winter cauliflower | Yellow | H | H | H | H |
| NEVIS (Seminis) | Late autumn cauliflower | White | H | Yellow | Yellow | White |
| NOMINOE (OBS) | late autumn cauliflower | Yellow | Yellow | Yellow | H | H |
| CEVELINE (Ryk Zwaan) | Summer cauliflower | Yellow | Yellow | Yellow | Yellow | Yellow |
| OPAAL (Ryk Zwaan) | Summer cauliflower | Yellow | Yellow | Yellow | Yellow | Yellow |
| CHAMBORD (Ryk Zwaan) | Summer cauliflower | Yellow | Yellow | Yellow | Yellow | Yellow |
| ABRUZZI (Seminis) | winter cauliflower | White | Yellow | Yellow | Yellow | White |

TABLE 4-continued

| Variety (Company) | Segment | QTLO1 | QTLO2A | QTLO2B | QTLO7 | QTLO9 |
|---|---|---|---|---|---|---|
| ALBINO (Seminis) | winter cauliflower | White | Yellow | White | Yellow | H |
| AMIATA (Seminis) | late autumn cauliflower | H | Yellow | Yellow | H | White |
| ARMSTRONG (Seminis) | Summer cauliflower | H | Yellow | Yellow | Yellow | H |
| BALDO (Seminis) | Summer cauliflower | H | Yellow | Yellow | Yellow | White |
| CADAL (Seminis) | winter cauliflower | Yellow | H | Yellow | H | White |
| CONERO (Seminis) | Summer cauliflower | Yellow | Yellow | Yellow | Yellow | White |
| CORNELL (Seminis) | Summer cauliflower | Yellow | Yellow | Yellow | Yellow | White |
| FREEDOM (Seminis) | Summer cauliflower | H | Yellow | Yellow | Yellow | H |
| FREMONT (Seminis) | Summer cauliflower | H | Yellow | Yellow | Yellow | H |
| HERMON (Seminis) | Summer cauliflower | Yellow | Yellow | Yellow | Yellow | H |
| LATTAI (Seminis) | winter cauliflower | Yellow | H | Yellow | H | H |
| PREMATO (Seminis) | Summer cauliflower | Yellow | H | Yellow | H | Yellow |
| SASSO (Seminis) | winter cauliflower | White | Yellow | Yellow | White | White |
| SUBLIME (Seminis) (Company) | Summer cauliflower | H | Yellow | Yellow | Yellow | H |
| VINSON (Seminis) | Summer cauliflower | H | Yellow | Yellow | Yellow | H |
| VULTURE (Seminis) | late autumn cauliflower | H | H | Yellow | Yellow | White |
| BAKER (Syngenta) | Summer cauliflower | Yellow | Yellow | Yellow | H | Yellow |
| BOULEN (Syngenta) | winter cauliflower | Yellow | Yellow | Yellow | H | White |
| BRODEN (Syngenta) | winter cauliflower | Yellow | H | Yellow | White | White |
| CLAPTON (Syngenta) | Summer cauliflower | Yellow | H | Yellow | Yellow | H |
| CLEMEN (Syngenta) | winter cauliflower | Yellow | White | Yellow | H | White |
| DIAMEN (Syngenta) | winter cauliflower | H | White | Yellow | Yellow | White |
| LECANU (Syngenta) | Summer cauliflower | Yellow | Yellow | Yellow | Yellow | H |
| LORIEN (Syngenta) | winter cauliflower | H | H | Yellow | Yellow | White |
| MAGELLAN (Syngenta) | Summer cauliflower | Yellow | Yellow | Yellow | Yellow | Yellow |

Example 10. Development of Progeny Lines

Progeny for the four lines provided above are produced and analyzed using markers QTL01, QTLO2a, QTL02b, QTL07 and QTL09 as discussed above.

Lines of CLP/NY6633 (O2:310-2) are used in replication trials and segregates for the QTLO2b marker. Lines derived from 02:310-2 (04:318-1) are selected and are homozygous white for all of the QTL markers. The results of the marker analysis are provided below in Table 5.

Lines of CLP/NY6633/9/FRE (03:259-1) are used in replication trials. Two progeny lines of 03:259-1 are obtained, 04:296-2 and 04:369-2. Plants of both of these lines contain the yellow allele for marker QTL09. Marker analysis results are also provided in Table 5 below.

Lines of 1BCSS/CLP/NY6633 (03:298-3) are also used in replication trials as described above. This line segregates for marker QTLO1. Two progeny lines are obtained, 04:476-1 and 04:476-3 also segregate or contain the yellow allele for marker QTLO1, and all are segregating for marker QTLO9. Marker analysis results are also provided in Table 5.

Lines of CLP/NY6633/9/FRE/CLP/NY6633/HOCE (356-1KNO) are used in replication trials as described above. This line segregates for marker QTLO2b. Three progeny lines are obtained, 04:563-1, 04:563-2 and 04:563-3. Two of the progeny lines, 04:563-1 and 04:563-2 segregate for marker QTLO2b, while line 04:563-3 is homozygous white at marker QTLO2b. However, line 04:563-3 segregates for marker QTLO2a. Marker analysis results are also provided in Table 5.

TABLE 5

| plant | QTLO1 | QTLO2a | QTLO2b | QTLO9 | QTLO7 |
|---|---|---|---|---|---|
| 02:310-2,1 | White | White | H | White | White |
| — | — | — | — | — | |

TABLE 5-continued

| plant | QTLO1 | QTLO2a | QTLO2b | QTLO9 | QTLO7 |
|---|---|---|---|---|---|
| 02:310-2,3 | White | White | Yellow | White | White |
| 02:310-2,4 | White | — | Yellow | White | White |
| 02:310-2,5 | White | White | H | White | White |
| 02:310-2,6 | White | White | Yellow | White | White |
| 02:310-2,7 | White | White | White | White | White |
| 02:310-2,8 | White | White | White | White | White |
| 02:310-2,9 | White | White | H | White | White |
| 02:310-2,10 | White | White | H | White | White |
| 04:348-1,1 | White | White | White | White | White |
| 04:348-1,2 | White | — | White | White | White |
| 04:348-1,3 | White | White | White | White | White |
| 04:348-1,4 | White | White | White | White | White |
| 04:348-1,5 | White | White | White | White | White |
| 04:348-1,6 | White | White | White | White | White |
| 04:348-1,7 | White | White | White | White | White |
| 04:348-1,8 | White | White | White | White | White |
|  | — | — | — | — | — |
|  | — | — | — | — | — |
| 03:259-1,1 | White | White | White | Yellow | White |
| 03:259-1,2 | White | White | White | Yellow | White |
| 03:259-1,3 | White | White | White | Yellow | White |
| 03:259-1,4 | White | White | White | Yellow | White |
| 03:259-1,5 | White | White | White | Yellow | White |
| 03:259-1,6 | White | White | White | Yellow | White |
| 03:259-1,7 | White | White | White | Yellow | White |
| 03:259-1,8 | — | — | White | — | — |
|  | — | — | — | — | — |
| 04:296-2,1 | White | White | White | — | White |
| 04:296-2,2 | White | White | White | Yellow | White |
| 04:296-2,3 | White | White | White | Yellow | White |
| 04:296-2,4 | White | White | White | Yellow | White |
| 04:296-2,5 | White | White | White | Yellow | White |
| 04:296-2,6 | White | White | White | Yellow | White |
| 04:296-2,7 | White | White | White | Yellow | White |
| 04:296-2,8 | White | White | White | Yellow | White |
|  | — | — | — | — | — |
|  | — | — | — | — | — |
| 04:369-2,1 | White | White | White | Yellow | White |
| 04:369-2,2 | White | White | White | Yellow | White |
| 04:369-2,3 | White | White | White | Yellow | White |
| 04:369-2,4 | White | White | White | Yellow | White |
| 04:369-2,5 | White | White | White | Yellow | White |
| 04:369-2,6 | White | White | White | Yellow | White |
| 04:369-2,7 | White | White | White | Yellow | White |
| 04:369-2,8 | White | White | White | Yellow | White |
| 04:369-2,9 | White | White | White | Yellow | White |
| 04:369-2,10 | White | White | White | Yellow | White |
| 04:476-1,1 | H | White | White | Yellow | White |
| 04:476-1,2 | White | White | White | Yellow | White |
| 04:476-1,3 | H | White | White | H | White |
| 04:476-1,4 | H | White | White | H | White |
| 04:476-1,5 | H | White | White | H | White |
| 04:476-1,6 | H | White | White | Yellow | White |
| 04:476-1,7 | H | White | White | H | White |
| 04:476-1,8 | H | White | White | H | White |
| 04:476-1,9 | H | White | White | Yellow | White |
| 04:476-1,10 | H | White | White | H | White |
| 04:476-3,1 | Yellow | White | White | H | White |
| 04:476-3,2 | Yellow | White | White | White | White |
| 04:476-3,3 | Yellow | White | White | H | White |
| 04:476-3,4 | Yellow | White | White | Yellow | White |
| 04:476-3,5 | Yellow | White | White | H | White |
| 04:476-3,6 | Yellow | White | White | White | White |
| 04:476-3,7 | Yellow | White | White | Yellow | White |
| 04:476-3,8 | Yellow | White | White | H | White |
| 04:476-3,9 | Yellow | White | White | White | White |
| 04:476-3,10 | Yellow | White | White | H | White |
| 03:298-3,1 | H | White | White | Yellow | White |
| 03:298-3,2 | H | White | White | Yellow | White |
| 03:298-3,3 | Yellow | White | White | H | White |
| 03:298-3,4 | White | White | White | Yellow | White |
| 03:298-3,5 | Yellow | White | White | H | White |
| 03:298-3,6 | Yellow | White | White | Yellow | White |
| 03:298-3,7 | H | White | White | Yellow | White |
| 03:298-3,8 | White | White | White | Yellow | White |
|  | — | — | — | — | — |
|  | — | — | — | — | — |
| 356-1KNO3,1 | White | White | H | White | White |
| 356-1KNO3,2 | White | White | White | White | White |
| 356-1KNO3,3 | White | White | Yellow | White | White |
| 356-1KNO3,4 | White | White | H | White | White |
| 356-1KNO3,5 | White | White | H | White | White |
| 356-1KNO3,6 | White | White | White/H | White | White |
| 356-1KNO3,7 | White | White | Yellow | White | White |
| 356-1KNO3,8 | White | White | H | White | White |
|  | — | — | — | — | — |
| 04:563-1,1 | White | White | White | White | White |
| 04:563-1,2 | White | White | Yellow | White | White |
| ED37 | Yellow | Yellow | Yellow | Yellow | Yellow |
| NY66 | White | White | White | White | White |
| H | H | H | H | H | H |
| TE | — | — | — | — | — |
| 04:563-1,3 | White | White | White | White | White |
| 04:563-1,4 | White | White | White | White | White |
| 04:563-1,5 | White | White | White | White | White |
| 04:563-1,6 | White | White | White | White | White |
| 04:563-1,7 | White | White | White | White | White |
| 04:563-1,8 | White | White | White | White | White |
| 04:563-1,9 | White | White | Yellow | White | White |
| 04:563-1,10 | White | White | H | White | White |
| 04:563-2,1 | White | White | White | White | White |
| 04:563-2,2 | White | White | White | White | White |
| 04:563-2,3 | White | White | H | White | White |
| 04:563-2,4 | White | White | White | White | White |
| 04:563-2,5 | White | White | H | White | White |
| 04:563-2,6 | White | White | H | White | White |
| 04:563-2,7 | White | White | White | White | White |
| 04:563-2,8 | White | White | White | White | White |
| 04:563-2,9 | White | White | White | White | White |
| 04:563-2,10 | White | White | H | White | White |
| 04:563-3,1 | White | H | White | White | White |
| 04:563-3,2 | White | White | — | White | White |
| 04:563-3,3 | White | H | White | White | White |
| 04:563-3,4 | White | H | White | White | White |
| 04:563-3,5 | White | White | White | White | White |
| 04:563-3,6 | White | H | White | White | White |
| 04:563-3,7 | White | Yellow | White | White | White |
| 04:563-3,8 | White | White | White | White | White |
| 04:563-3,9 | White | — | White | White | White |
| 04:563-3,10 | White | — | White | White | — |

What is claimed:

1. A cauliflower plant, wherein said cauliflower plant comprises a curd, said curd having a color score of less than C4 on a Centre Technique Interprofessionnel des Fruits et Legumes (Ctifl) cauliflower color chart, wherein said cauliflower plant comprises a homozygous brilliant white QTLO2a allele, a homozygous brilliant white QTLO1 allele, and a homozygous brilliant white QTLO7 allele.

2. The cauliflower plant of claim 1, wherein said color score is obtained at the time of harvest after growth without covering for a period of about 1 day, 2 days, 3 days, 4 days, 5 days, 6 days, 7 days, 8 days, 9 days, 10 days, 1 week, 2 weeks, 3 weeks, or 4 weeks.

3. A tissue culture of cells derived from the cauliflower plant of claim 1, wherein said tissue culture of cells is from a tissue selected from the group consisting of leaf, pollen, embryo, root, root tip, anther, flower, bud, curd, and meristem.

4. The cauliflower plant of claim 1, wherein said color score is obtained at the time of harvest and wherein said curd weighs at least 350 grams.

5. The cauliflower plant of claim 1, wherein said cauliflower plant further comprises at least one favorable curd characteristic selected from the group consisting of a diameter of at least 15 centimeters, a weight of at least 700 grams, an amount of hairiness between absent and intermediate, and an amount of bracting between absent and intermediate.

6. The cauliflower plant of claim 1, wherein said cauliflower plant is a hybrid.

7. The cauliflower plant of claim 1, wherein said color score of less than C4 on a Ctifl cauliflower color chart persists after five days of storage at 5° C.

8. The cauliflower plant of claim 1, wherein said curd has a color score on a Ctifl cauliflower color chart selected from the group consisting of less than or equal to C3, less than or equal to C2, and a color score of 1.

9. The cauliflower plant of claim 1, wherein said brilliant white QTLO2a allele is identifiable by a nucleic acid marker within about 10 cM of a nucleic acid molecule comprising SEQ ID NO: 6, said brilliant white QTLO1 allele is identifiable by a nucleic acid marker within about 10 cM of a nucleic acid molecule comprising SEQ ID NO: 1, and said brilliant white QTLO7 allele is identifiable by a nucleic acid marker within about 10 cM of a nucleic acid molecule comprising SEQ ID NO: 14.

10. The cauliflower plant of claim 1, wherein said brilliant white QTLO2a allele is identifiable by a nucleic acid marker within about 5 cM of a nucleic acid molecule comprising SEQ ID NO: 6, said brilliant white QTLO1 allele is identifiable by a nucleic acid marker within about 5 cM of a nucleic acid molecule comprising SEQ ID NO: 1, and said brilliant white QTLO7 allele is identifiable by a nucleic acid marker within about 5 CM of a nucleic acid molecule comprising SEQ ID NO: 14.

11. A cauliflower seed capable of producing a cauliflower plant comprising a curd, said curd having a color score of less than C4 on a Centre Technique Interprofessionnel des Fruits et Legumes (Ctifl) cauliflower color chart, and wherein said cauliflower plant comprises a homozygous brilliant white QTLO2a allele, a homozygous brilliant white QTLO1 allele, and a homozygous brilliant white QTLO7 allele.

12. The cauliflower seed of claim 11, wherein said homozygous brilliant white QTLO2a allele is identifiable by a nucleic acid marker within about 10 cM of a nucleic acid molecule comprising SEQ ID NO: 6, said homozygous brilliant white QTLO1 allele is identifiable by a nucleic acid marker within about 10 cM of a nucleic acid molecule comprising SEQ ID NO: 1, and said homozygous brilliant white QTLO7 allele is identifiable by a nucleic acid marker within about 10 cM of a nucleic acid molecule comprising SEQ ID NO: 14.

13. The cauliflower seed of claim 11, wherein said curd has a color score on a Ctifl cauliflower color chart selected from the group consisting of less than or equal to C3, less than or equal to C2, and a color score of 1.

14. The cauliflower seed of claim 11, wherein said curd weighs at least 350 grams, at least 400 grams, at least 500 grams, at least 600 grams, or at least 700 grams.

15. The cauliflower seed of claim 11, wherein said color score of less than C4 on a Ctifl cauliflower color chart persists after five days of storage at 5° C.

16. A container comprising the cauliflower seeds of claim 11.

17. A method of producing a cauliflower plant, the method comprising:
   planting a cauliflower seed; and
   growing said cauliflower seed into a cauliflower plant;
   wherein said cauliflower plant comprises a curd, said curd having a color score of less than C4 on a Centre Technique Interprofessionnel des Fruits et Legumes (Ctifl) cauliflower color chart, and wherein said cauliflower plant comprises a homozygous brilliant white QTLO2a allele, a homozygous brilliant white QTLO1 allele, and a homozygous brilliant white QTLO7 allele.

* * * * *